United States Patent [19]

Afonso et al.

[11] Patent Number: 5,608,067

[45] Date of Patent: Mar. 4, 1997

[54] 4-SUBSTITUTED PYRAZOLOQUINOLINE DERIVATIVES

[76] Inventors: Adriano Afonso, 10 Woodmere Rd., West Caldwell, N.J. 07006; Joseph M. Kelly, 112 Princeton Rd., Parlin, N.J. 08859; Samuel Chackalamannil, 79 Stratford Rd., East Brunswick, N.J. 08816

[21] Appl. No.: 234,695

[22] Filed: Apr. 28, 1994

Related U.S. Application Data

[63] Continuation-in-part of Ser. No. 164,179, Dec. 9, 1993, abandoned.

[51] Int. Cl.$^6$ ................................................. C07D 471/04
[52] U.S. Cl. ..................... 546/82; 544/126; 514/232.8; 514/293
[58] Field of Search ................... 546/82; 514/293, 514/232.8; 544/126

[56] References Cited

U.S. PATENT DOCUMENTS

| | | | |
|---|---|---|---|
| 3,600,393 | 8/1971 | Graeve et al. | 260/286 |
| 3,790,573 | 2/1974 | Blackburn et al. | 260/256.4 |
| 3,790,576 | 2/1974 | DeWald | 260/286 R |
| 4,013,665 | 3/1977 | Crenshaw | 260/288 |
| 4,283,393 | 8/1981 | Field et al. | 424/180 |
| 4,745,115 | 5/1988 | Markwell et al. | 514/226.8 |
| 4,753,950 | 6/1988 | Shutske et al. | 514/291 |
| 4,920,128 | 4/1990 | Bell et al. | 514/293 |

FOREIGN PATENT DOCUMENTS

| | | |
|---|---|---|
| 233445 | 7/1984 | Czechoslovakia . |
| 235177 | 9/1984 | Czechoslovakia . |
| 252340 | 1/1989 | Czechoslovakia . |
| 273176 | 11/1986 | European Pat. Off. . |
| 2140787 | 2/1983 | German Dem. Rep. . |
| 1152410 | 8/1963 | Germany . |
| 1445719 | 1/1969 | Germany . |
| 3204126 | 2/1982 | Germany . |

OTHER PUBLICATIONS

Stein et al, J. Med. Chem., 13(1), pp. 153–155 Jan. 1970.
Radl et al, Czechoslovak Pharmacy 34(3–4), pp. 119–122, month not available (1985) and English translation.
Crenshaw, Journal of Medicinal Chemistry, vol. 19, No. 2, pp. 262–275 month not available 1976.
Radl et al, Czechoslavak Pharmacy 33(10), pp. 429–432, Month Not Available (1984) and English translation.
CA 756 f and g, vol. 61. 1964.
BIOSIS/CAS Selects Antiviral Agents Issue 6, 110:75485k 1989.
Czech Pharmacy 34(9), pp. 383–385, Month Not Available (1985) English translation only.
Radl et al, Collection Czech Commun. (vol. 51) 1986, pp. 1692–1693, Month Not Available and English translation.
CA 9 38293 1915.
Radl et al, Czech Pharmacy, 35(3) pp. 105–109 Month Not Available (1986), and English translation.

*Primary Examiner*—Johann Richter
*Assistant Examiner*—Laura L. Stockton
*Attorney, Agent, or Firm*—Matthew Boxer; John J. Maitner

[57] ABSTRACT

Disclosed herein are compounds of the formula

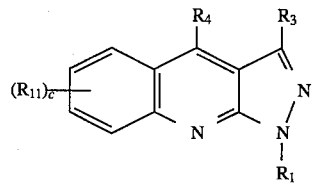

wherein $R_1$, $R_3$, $R_4$, $R_{11}$, and c are as set forth herein are described. These compounds are useful as agents for the treatment of mammals infected with herpes group virus. Certain of these compounds are useful as antitumor agents.

4 Claims, No Drawings

4-SUBSTITUTED PYRAZOLOQUINOLINE DERIVATIVES

BACKGROUND OF THE INVENTION

This application is a continuation-in-part of 08/164,179, filed 12/9/93, now abandoned.

This invention relates to 4-substituted 3-alkyl-pyrazolo[3,4-b]quinoline compounds, pharmaceutical compositions containing them and methods of treating patients afflicted with a herpes group virus infection by use of such compositions.

There are four separate herpes group viruses which infect and cause disease in humans. These four viruses are (1) the herpes simplex virus types 1 and 2 (HSV-1 and HSV-2, respectively); (2) the cytomegalovirus (CMV); (3) varicella-zoster (VZ) virus; and (4) the Epstein-Barr (EB) virus.

Examples of diseases associated with HSV-1 and HSV-2 infections include herpes labialis, genital herpes (herpes progenitalis), neonatal herpes, herpetic keratitis, eczema herpecticum, disseminated herpes, occupational herpes, herpectic gingivostomatitis, meningitis (aseptic), and encephalitis.

The VZ virus is associated with chicken-pox (varicella) and shingles (zoster) in humans.

The CMV is wide spread in humans and numerous other mammals. A great majority of human CMV infections are subclinical; that is, the primary infection occurs with no signs or symptoms. An exception to this is a congenital infection which occasionally gives rise to cytomegalic inclusion body disease in infants. There is also a mononucleosis-like syndrome caused by the virus.

A great majority of serious cases due to CMV infections come from recurring infections in immuno-compromised individuals, such as in transplant patients and in cancer patients. It has been estimated that silent CMV infections have occurred in a majority of humans by the time adulthood is reached.

Examples of drugs used to treat herpes infections include: (1) IUDR (5'-iodo-2'-deoxyuridine); (2) Ara-C (1-[beta-D-arabinofuranosyl]cytosine); (3) Ara-A (9-beta-D-arabinofuranosyladenine); and (4) Acyclovir (9-[(2-hydroxyethoxy)methyl]guanine). Also Haines et al. (U.S. Pat. No. 4,757,088 issued Jul. 12, 1988) discloses that lidocaine (2-(diethylamino)-N-(2,6-dimethylphenyl)acetamide) is an antiviral agent in cell culture against HSV-1 and HSV-2, and is able to treat herpes virus infections of mammals. Haines et al. also disclose that lidocaine is particularly effective in the treatment of HSV oral and genital lesions in humans. According to Haines et al., the addition of panthothenic acid or its alcohol and salt forms, dexpanthenol and pantothenate, respectively, to lidocaine or lidocaine hydrochloride significantly enhances and antiviral activity of those drugs.

There is still a need for antiviral compounds exhibiting activity against the herpes group viruses, especially against HSV-1 and HSV-2.

SUMMARY OF THE INVENTION

The invention relates to compounds of the formula

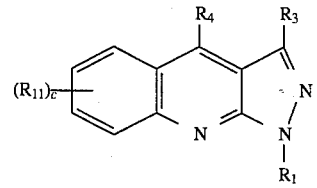

or pharmaceutically acceptable salts thereof,
wherein
$R_1$ is H, amino($C_1$–$C_8$)alkanoyl, ($C_2$–$C_8$)alkenyl, ($C_1$–$C_8$)alkoxycarbonyl, ($C_1$–$C_4$)alkoxycarbonyl($C_1$–$C_8$)alkyl, —CO—$R_{15}$ wherein $R_{15}$ is ($C_1$–$C_8$)alkyl substituted by $NH_2$ or —$CH_2$—$NHR_{16}$ wherein $R_{16}$ is ($C_1$–$C_4$)alkyl;

$R_3$ is ($C_1$–$C_8$)alkyl, or H $R_4$ is $NR_aR_b$, —$NR_a(CH_2)_nQR_9$, —$NHCH_2COR_c$, wherein $R_a$ and $R_b$ are each independently H, mono or dihydroxyphenyl, ($C_3$–$C_8$) straight or branched alkyl substituted by at least one OH, or ($C_1$–$C_8$)alkyl, $R_c$ is OH, L-amino acid residue, —$NH(CH_2)_rX$ wherein X is

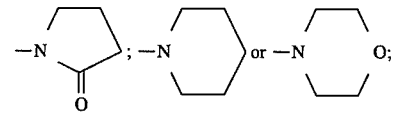

and r is 1 to 3; or $R_a$ and $R_b$ taken together with N form

wherein T is O, —$NR_a$—, —CO—, —$CONR_a$—, —S— or a direct bond and m is 1, 2 or 3;

Q is —O—, —$NR_a$—, —S—, —CO—, —$CONR_a$—, —COO— or a direct bond;

n is 2 to 6;

$R_9$ is H, M+, ($C_1$–$C_8$)alkyl, or $(CH_2)_pQR_{10}$
wherein $R_{10}$ is H, ($C_1$–$C_8$)alkanoyl, ($C_1$–$C_8$)alkyl, or a silyl protecting group; p is 1 to 5; M+ is a pharmaceutically acceptable cation; and Q is as defined hereinabove;

c is 1, 2, 3, 4; and $R_{11}$ is ($C_1$–$C_8$)alkoxy, benzyloxy or OH when c is 1 and when c is 2, 3 or 4, $R_{11}$ is ($C_1$–$C_8$)alkyl, and the remaining $R_{11}$ are H, halogen, OH ($C_1$–$C_8$)alkoxy, or ($C_1$–$C_8$)alkyl.

These compounds are antiviral agents.

Of these, preferred are compounds wherein $R_2$ is —$OCH_3$.

Of these, preferred are compounds wherein $R_4$ is —$NH(CH_2)_2O(CH_2)_2OH$.

Of these, preferred are compounds wherein $R_4$ is —$NH(CH_2)_2O(CH_2)_2OCOCH_3$.

Of these, preferred are compounds wherein $R_4$ is

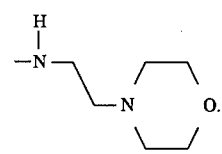

Of these, preferred are those wherein $R_1$ is H.
Of these preferred are those wherein $R_1$ is —$C(O)OC(CH_3)_3$.

Of these, preferred are those wherein $R_1$ is a natural α-amino acid.
The invention also relates to compounds of the formula:
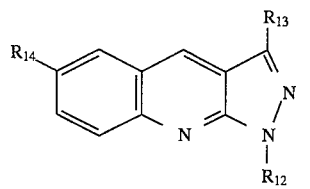  II
wherein $R_{12}$ is —CO— $R_{15}$, wherein $R_{15}$ is $(C_1-C_8)$ alkyl substituted by $NH_2$ or —$CH_2$—$NHR_{16}$ wherein $R_{16}$ is $(C_1-C_4)$ alkyl;
$R_{13}$ is $(C_1-C_8)$ alkyl; and
$R_{14}$ is $(C_1-C_8)$ alkoxy.
Exemplary of compounds of the invention are
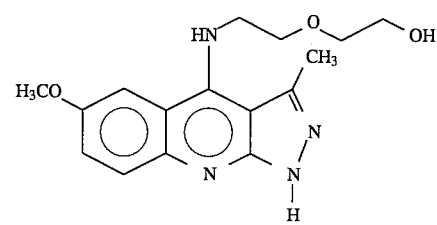 (1)
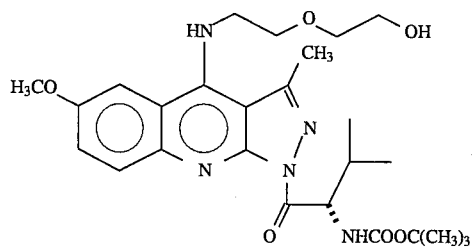 (2)
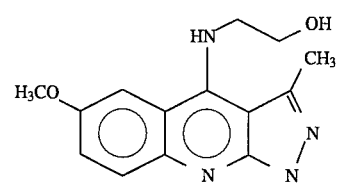 (3)
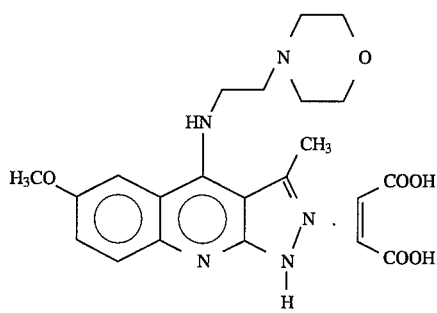 (4)
-continued
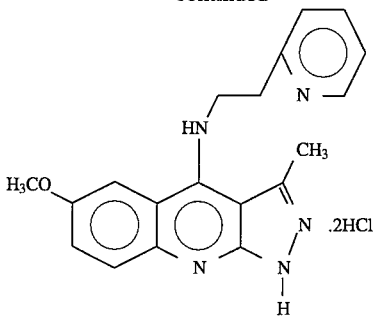 (5)
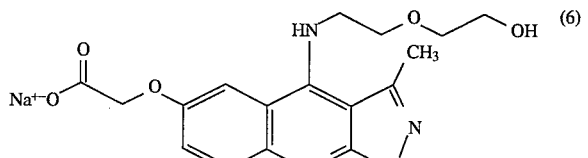 (6)
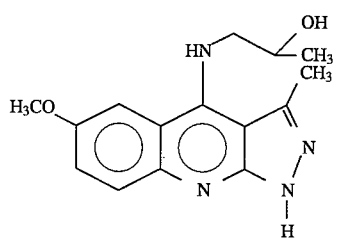 (7)
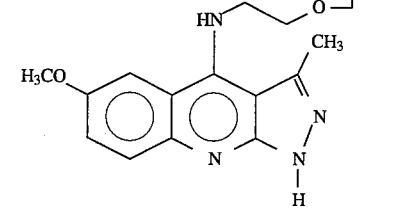 (8)
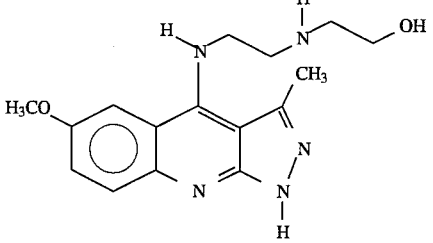 (9)
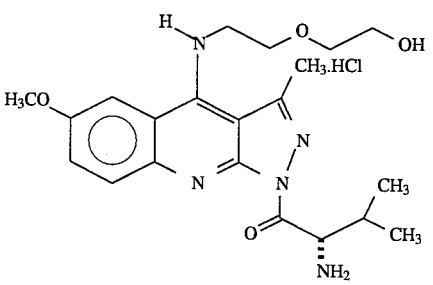 (10)

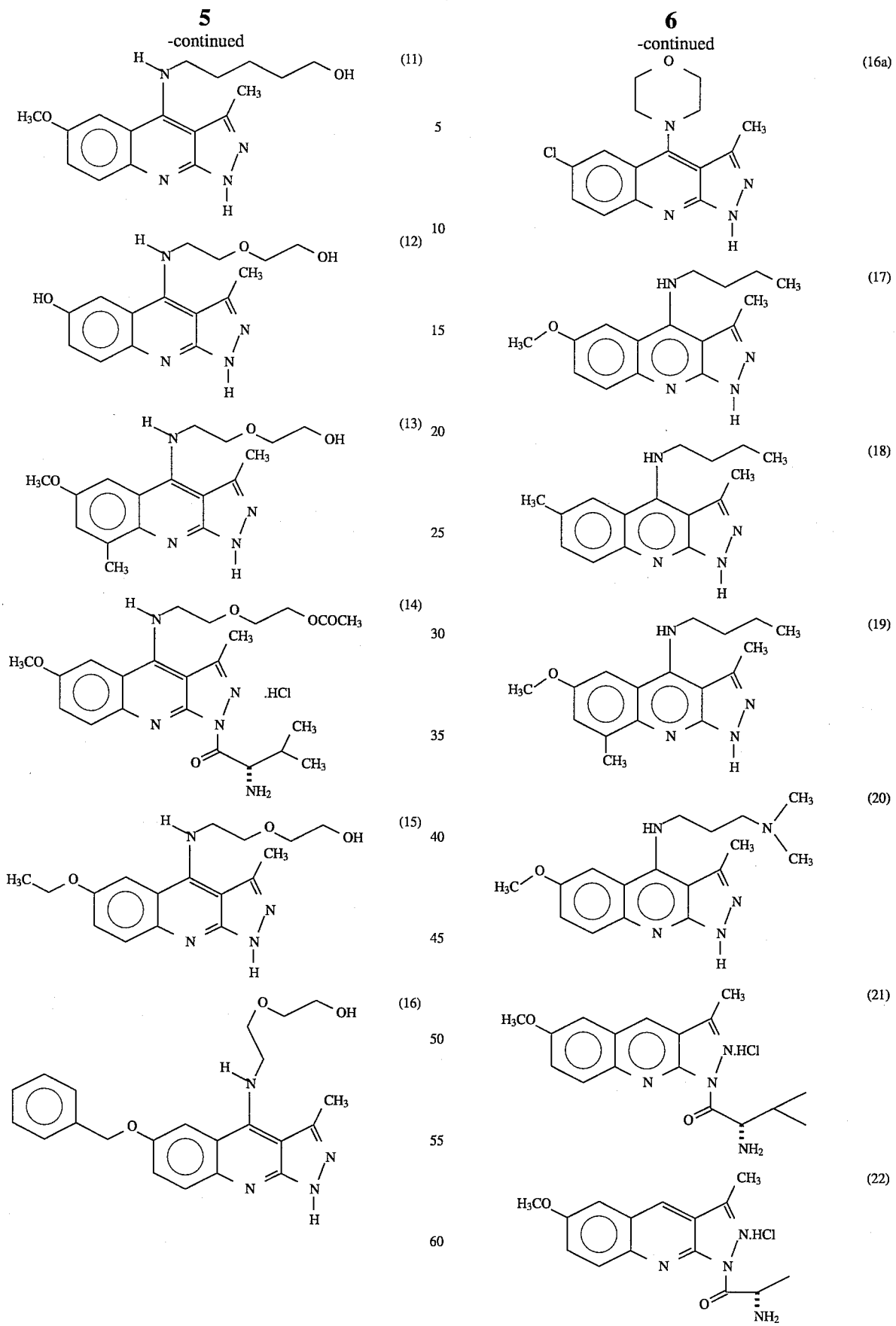

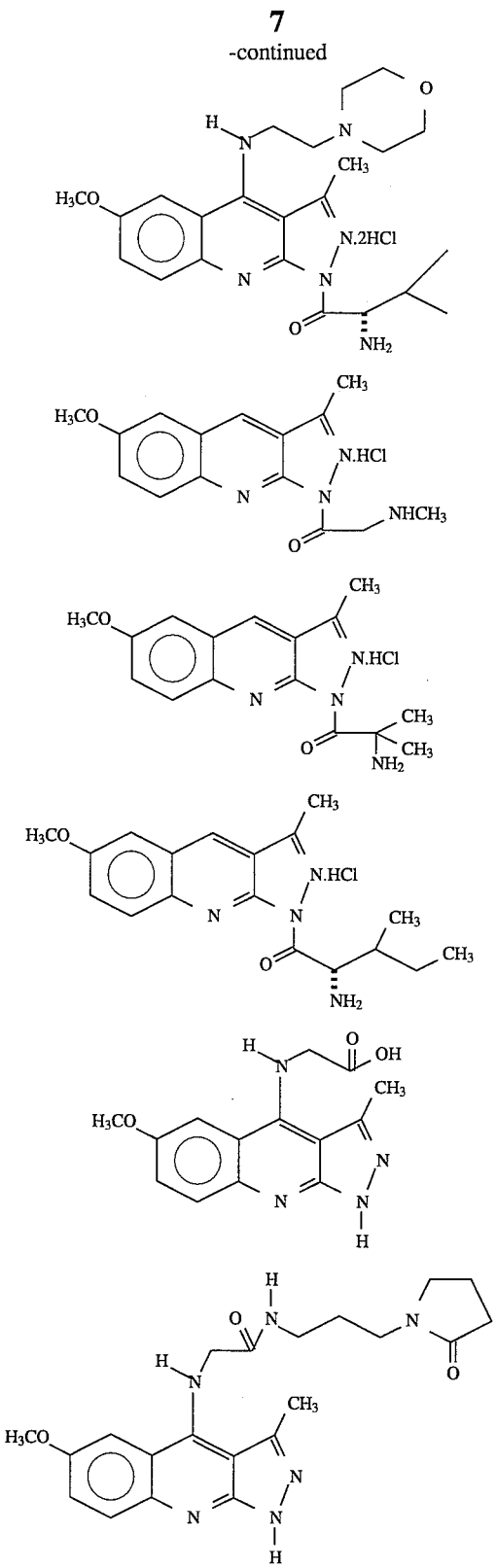
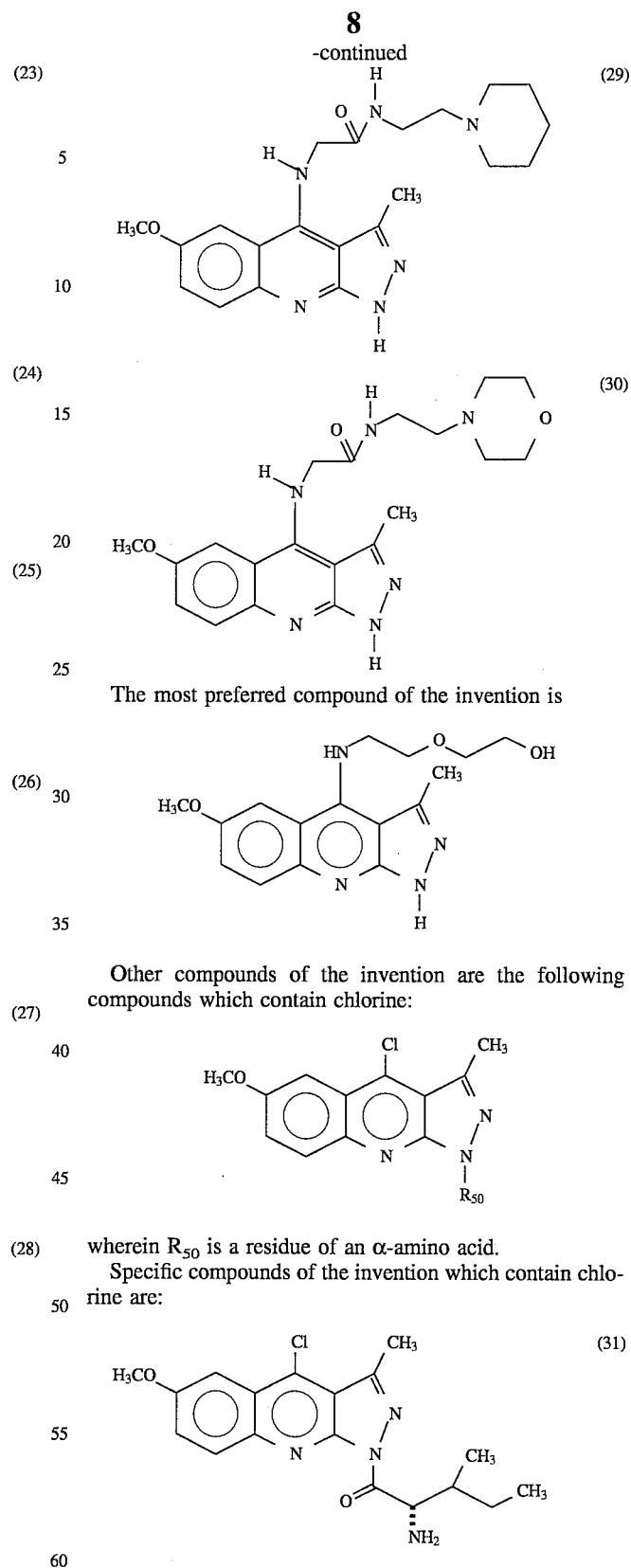
The most preferred compound of the invention is
Other compounds of the invention are the following compounds which contain chlorine:
wherein $R_{50}$ is a residue of an α-amino acid.
Specific compounds of the invention which contain chlorine are:
FAB MASS SPEC 361 (M+1)+

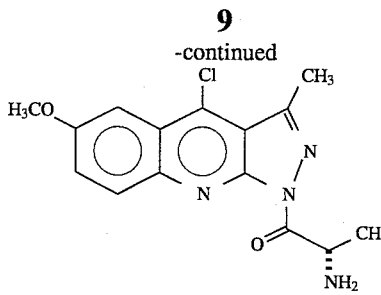

FAB MASS SPEC 319 (M+1)⁺

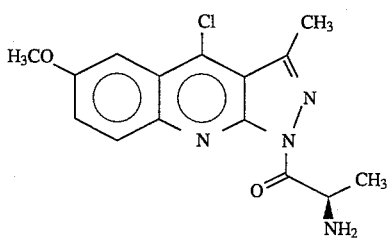

and

FAB MASS SPEC 319 (M+1)⁺ or a pharmaceutically acceptable salt thereof.

The present invention also provides pharmaceutical compositions for treating patients afflicted with a herpes group virus which comprises an anti-herpes effective amount of a compound of formulas I or II and a pharmaceutically acceptable carrier therefor as well as methods of treating a patient afflicted with a herpes group virus which comprises administering to said patient an anti-herpes effective amount of a compound of formulas I or II.

Certain compounds of the invention are also active as agents in the treatment of tumors. Therefore, the present invention also provides pharmaceutical compositions which comprise certain compounds of the invention, and which compositions are useful for treating patients afflicted tumors. The present invention also provides methods of treating a patient having tumors, which methods comprise administering to said patient an antitumor effective amount of certain compounds of the invention.

DETAILED DESCRIPTION OF THE INVENTION

As used herein, the term "($C_1$–$C_8$) alkyl" refers to straight and branched chain hydrocarbon groups of 1 to 6 carbon atoms, such as methyl, ethyl, n-, and iso-propyl, n-, sec- and tert-butyl, n-, sec-, iso-, tert- and neo-pentyl, n-, sec-, iso-, tert-hexyl and n-, sec-, iso-, tert-, and neo-heptyl and n-, sec-, iso-, tert-, and neo-octyl. Alternatively, alkyl with lower numbers of carbon atoms are also referred to in the specification. For example, the term "($C_1$–$C_3$) alkyl" refers to straight and branched chain hydrocarbon groups of 1 to 3 carbon atoms, such as methyl, ethyl, n-, and iso-propyl. The preferred ($C_1$–$C_8$)alkyl is methyl.

The term "($C_1$–$C_8$) alkanoyl" refers to straight and branched chain alkanoyl groups having 1 to 8 carbon atoms such as formyl, acetyl, propanoyl, butanoyl, 2-methylpropanoyl, 3-methylpropanoyl, pentanoyl, 2-methylbutanoyl, 3-methylbutanoyl, 4-methylbutanoyl, hexanoyl, 2-methylpentanoyl, 3-methylpentanoyl, 4-methylpentanoyl, 5-methylpentanoyl, heptanoyl, 3-methylheptanoyl, octanoyl, 2-ethylhexanoyl and the like. Acetyl is preferred.

The term "($C_2$–$C_8$) alkenyl" refers to straight and branched chain alkenyl groups of 2 to 8 carbons including —$C_2H_3$—, —$C_3H_5$ —C($CH_3$)=$CH_2$, —$C_4H_7$, and $C_6H_{11}$.

The term "residue of an α-amino acid" means an α-amino acid which lacks an OH group on the carboxyl group of the amino acid. Such an α-amino acid is bonded by means of a peptide bond through the carboxyl group directly to the nitrogen atom at the 1-position of the pyrazoloquinoline ring. An example of a residue of an α-amino acid is found in compound (31) shown just below and is indicated by the arrow:

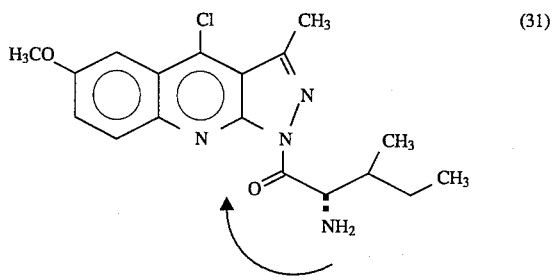

Exemplary of α-amino acids are glycine, alanine, valine, leucine, isoleucine, phenylalanine, proline, serine, threonine, tyrosine, cysteine, cystine, methionine, aspartic acid, glutamic acid, asparagine, glutamine, tryptophan, lysine, arginine, and histidine.

The term "pharmaceutically acceptable salt" refers to maleates, hydrochlorides, hydrobromides, sulfates, phosphates and tartrates. One skilled in the art will realize that acid addition salts of the compounds of the invention may be made with such salts whenever a basic functionality is present in a particular compound of the invention.

The term "a pharmaceutically acceptable cation" refers to sodium, potassium and the like.

The term "amino($C_1$–$C_8$)alkanoyl" includes α-aminoacyl residues derived from known L- and D- amino acids.

Certain compounds of this invention may exist in isomeric forms. The invention contemplates all such isomers both in pure form and in admixture, including racemic mixtures.

Certain compounds of the invention can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

The compounds of this invention exhibit anti-HSV activity in two art recognized in vitro assays: (1) a beta Galactosidase Assay and (2) a Plaque Reduction Assay. $IC_{50}$ values for the compounds of this invention in each assay were in the range of 1.0 to <10 mg/mL.

All of the compounds of the invention are useful as anti viral (herpes) agents. Certain compounds of the invention are useful as antitumor agents as well.

IN-VITRO ANTI-HSV ACTIVITY ASSAYS

The compound toxicity assay (3H-LEU), Plaque Reduction Assay for HSV Antiviral Activity (Plaque), and Transient Expression Assay for Effects Against HSV Early Gene Expression (βGalactosidase Assay or βgal) were carried out as set forth in U.S. Pat. No. 5,175,151 which is hereby incorporated by reference.

THE α-ACTIN ASSAY

The α-Actin assay or anti-tumor α-actin assay using stable cell lines was carried out as set forth in the applicants' copending application Ser. No. 08/164,238 now U.S. Pat.

No. 5,459,146 (Attorney's Docket No. IN0011-3) which is hereby incorporated by reference.

Test results for compounds of the invention in the above assays are reported below.

| Compound | βgal µg/ml | Plaque µg/ml | $^3$H—LEU µg/ml | α-actin µM range |
|---|---|---|---|---|
| (1) | 5 | N.T. | N.T. | 0.5–31 |
| (2) | N.T. | N.T. | N.T. | 1–10 |
| (3) | 1.3 | 2.3 | 8.2 | N.A. |
| (4) | 20 | 10 | 100 | N.T. |
| (5) | 1.0 | 7.50 | N.T. | N.T. |
| (6) | N.T. | N.T. | N.T. | 0.7–6.25 |
| (7) | N.T. | N.T. | N.T. | N.A. |
| (8) | N.T. | N.T. | N.T. | N.A. |
| (9) | N.T. | N.T. | N.T. | N.A. |
| (10) | N.T. | N.T. | N.T. | 0.7–6.26 |
| (11) | N.T. | N.T. | N.T. | N.A. |
| (13) | N.T. | N.T. | N.T. | 6.25–25 |
| (14) | N.T. | N.T. | N.T. | 1–10 |
| (15) | N.T. | N.T. | N.T. | 1–10 |
| (16) | N.T. | N.T. | N.T. | N.A. |
| (16a) | N.T. | N.T. | N.T. | N.A. |
| (17) | <3 | N.T. | 3.2 | N.A. |
| (18) | 3 | N.T. | 21.5 | 250–500 |
| (19) | 3 | N.T. | 21.5 | N.A. |
| (20) | 0.8 | N.T. | N.T. | N.T. |
| (21) | 0.2 | 20 | N.T. | 2–15 |
| (22) | 0.2 | 0.2 | N.T. | N.T. |
| (23) | 0.2 | 20 | N.T. | N.T. |
| (24) | 0.2 | 2.0 | N.T. | 4–31 |
| (25) | 0.2 | 20 | N.T. | N.T. |
| (26) | N.T. | N.T. | N.T. | 4–31 |
| (27) | 20 | N.T. | N.T. | N.T. |
| (28) | 2 | 20 | N.T. | N.T. |
| (29) | 6 | 20 | N.T. | N.T. |
| (30) | 2 | 20 | N.T. | N.T. |
| (31) | 0.2 | 0.8 | N.T. | N.T. |
| (32) | 1.8 | 0.2 | N.T. | N.T. |
| (33) | 0.5 | 0.2 | N.T. | N.T. |

As used herein N.A. means not active. N.T. means that the compound was not tested in the assay.

The above test results indicate that compounds of the invention were active as antiviral agents, and that certain compounds of the invention were active as antitumor agents.

The compounds of this invention may be prepared by the examples set forth herein, or by processes analogous to those of the examples set forth herein. Starting materials for preparing the compounds of this invention are either known, or may be made by known processes, or else the preparation of such starting materials are described herein.

The compounds of this invention can be administered in any number of conventional dosage forms, e.g., topical, oral, parenteral, rectal, transdermal, inhalation and the like. Oral or rectal dosage forms include capsules, tablets, pills, powders, cachets, and suppositories. Liquid oral dosage forms include solutions and suspensions. Parenteral preparations include sterile solutions and suspensions. Inhalation administration can be in the form of a nasal or oral spray, or by insufflation. Topical dosage forms can be creams, ointments, lotions, transdermal devices (e.g., of the conventional patch or matrix type) and the like.

The formulations and pharmaceutical compositions contemplated by the above dosage forms can be prepared with conventional pharmaceutically acceptable excipients and additives, using conventional techniques. Such pharmaceutically acceptable excipients and additives are intended to include carriers, binders, preservatives lubricants, etc.

Suitable pharmaceutical acceptable solid carriers are magnesium carbonate, magnesium stearate, talc, sugar, lactose, and the like. Capsules can be made wherein the active compound is inserted into pharmaceutically acceptable capsules as a carrier. The active compounds of this invention can be mixed with pharmaceutically acceptable excipients or be used in finely divided powder form without excipients for inclusion into the capsules. Similarly, cachets are included.

Liquid form preparations include solutions, suspensions and emulsions such as water or water-propylene glycol solutions for parenteral injection.

Formulations for topical application may include the above liquid forms, as well as creams, aerosols, sprays, dusts, powders, lotions and ointments which are prepared by combining an active ingredient according to this invention with conventional pharmaceutical acceptable diluents and carriers commonly used in topical dry, liquid, cream and aerosol formulations.

Lotions may be formulations with an aqueous or oil base and will, in general, also include one or more of pharmaceutically acceptable stabilizing agents, emulsifying agents, dispersing agents, suspending agents, thickening agents, coloring agents, perfumes and the like.

Powders may be formed with the aid of any suitable pharmaceutically acceptable powder base, e.g., talc, lactose, starch, etc. Drops may be formulated with an aqueous base or non-aqueous base also comprising one or more pharmaceutically acceptable dispersing agents, suspending agents, solubilizing agents, etc.

The topical pharmaceutical compositions may also include one or more preservatives or bacteriostatic agents, e.g., methyl hydroxybenzoate, propyl hydroxybenzoate, chlorocresol, benzalkonium chlorides, etc.

The topical pharmaceutical compositions may also contain an active compound of this invention in combination with other active ingredients such as antimicrobial agents, particularly antibiotics, anesthetics, analgesics and antipruritic agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit.

The compounds of this invention may also be deliverable transdermally for systemic distribution. The transdermal compositions can take the form of creams, lotions and/or emulsions and can be included in a transdermal patch of the matrix or reservoir type as are conventional in the art for this purpose.

The compounds of this invention may be administered by any conventional mode of administration by employing an antiviral effective amount of a compound of this invention for such mode. The dosages may be varied depending upon the requirements of the patient in the judgment of the attending clinician, the severity of the condition being treated and the particular compound being employed. Determination of the proper dosage for a particular situation is within the skill of the art. Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired.

Thus, depending on the mode, dosages of from about 0.1 to about 100 mg/kg of body weight per day may be administered to provide antiviral activity. For example, when administered orally doses of from about 20 to about 60 mg/kg of body weight may be used; and when administered parenterally, e.g., intravenously, dosages of from about 5 to about 20 mg/kg body weight may be used.

When administered topically, the amount of compound administered varies widely with the amount of skin being treated, as well as with the concentration of active ingredient applied to the affected area. Preferably, topical compositions contain from about 0.10 to about 10 percent by weight of the active ingredient and are applied as needed according to the judgment of the attending clinician. When administered rectally, the compounds of this invention may be administered in daily doses ranging from about 0.1 mg/kg to abut 100 mg/kg of body weight.

The dosage to be administered and the route of administration depends upon the particular compound used, the age and general health of the patient and the severity of the viral condition. Thus, the dose ultimately decided upon must be left to the judgment of a trained health-care practitioner.

Compounds (31), (32) and (33) may be made methods analogous to those set forth herein by using the following starting materials:

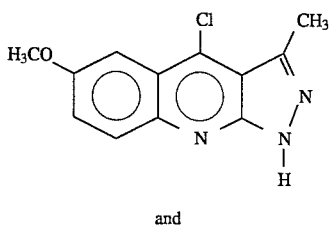

and

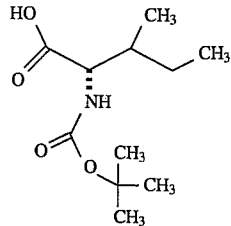

to obtain compound (31);

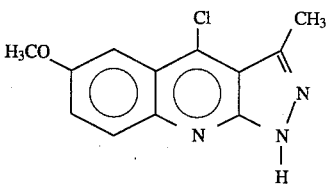

and

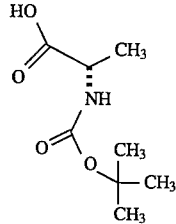

to obtain compound (31); and

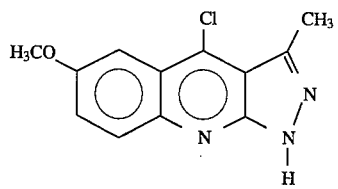

and

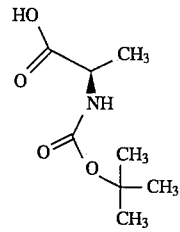

to obtain compound (33).

EXAMPLES

Starting materials for preparing the compounds of this invention are either known, or may be made by known processes, or else the preparation of such starting materials are described herein.

Example 1

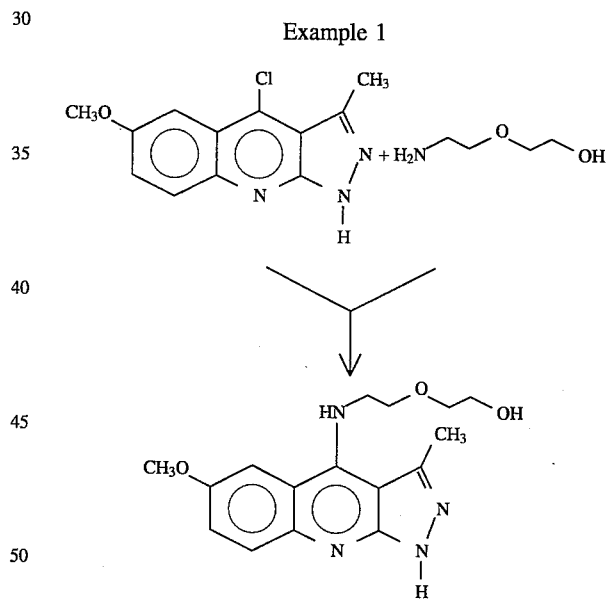

Sodium hydride (60% in oil, 60 mg, 1.49 mmol) was added to 2-(2-aminoethoxy)ethanol (5.0 ml, 49.8 mmol), then stirred 30 minutes at 20° C. 6-methoxy-4-chloro-3-methyl-1(H) pyrazolo-[3.4-b] quinoline (300 mg, 1.26 mmol) was added and so-formed reaction mixture was stirred at 110° C. overnight. The reaction mixture was cooled to 50° C. Water was added (15 ml). The reaction mixture was allowed cool to 20° C. The precipitated solid was filtered. The yellow powder was washed with water (20 ml), dried at 60° C./0.1 mm, chromatographed on silica gel and eluted from a column with 7% (v/v) methanol:methylene choride to produce the title compound as a yellow powder, (350 mg, 91.3% of theory). MS (CI m/e m$^+$1 (317) molecular formula $C_{16}H_{10}N_4O_3$. The starting chloride compound was prepared as described in example 3 of applicants' coponding application Ser. No. 08/164,178, now abandoned, (Attorney's Docket No. IN0011-1) which is hereby incorporated by reference.

The starting amine is known or may be prepared by known methods.

Example 2

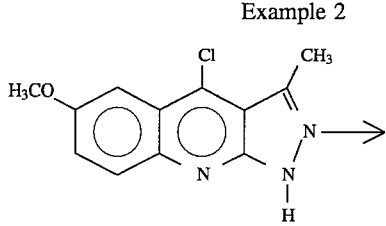

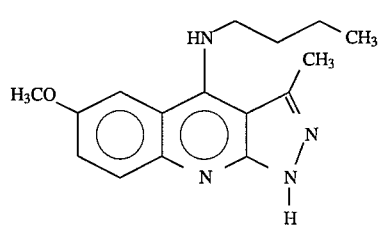

The chloride (3.0 g, 0.012 mole) was stirred in dimethylformamide (anhydrous, 100 ml) at 20° C., n-butylamine (7.0 ml, 0.07 mol) was added, followed by potassium carbonate (anhydrous, 0.028 mol), and the resulting mixture was stirred at 120° C. overnight. The reaction mixture was cooled to 50° C., and water (10 ml) was added dropwise. The precipitated solid was filtered, washed with water (50 ml), and dried at 60° C./0.2 mm to yield the product as yellow powder (2.5 g. 96.1% yield).

Example 3

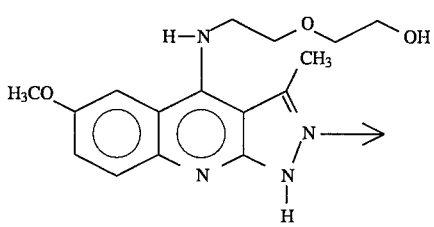

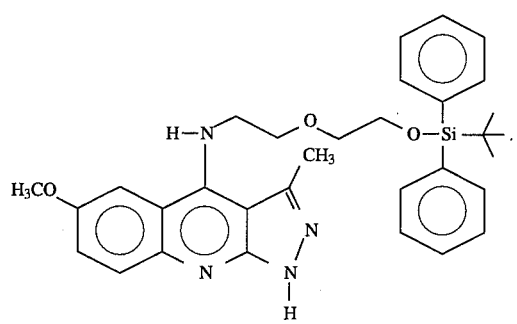

t-Butyl diphenyl silyl chloride(4.0 ml, 15.38 mmol) was added to a solution of 6-methoxy-4-[2-[2[(-hydroxyethoxy) ethyl)ethyl]amino]-3-methyl-1(H)-pyrazolo-[3,4-b]quinoline (4.0 g, 12.66 mmol) in dimethylformamide (50 ml) at 20° C. Imidazole (1.36 g, 20 mmol) was added immediately and the resulting solution was stirred overnight at 20° C. The solvent was evaporated under reduced pressure. The residue was extracted with methylene chloride (200 ml), and washed with water (100 ml) The organics were dried over magnesium sulfate, filtered, and the solvent was evaporated to yield an oil which was chromatographed on silica gel, eluting with 2% v/v methanol/methylene chloride to yield the title product as a yellow solid.

Example 4

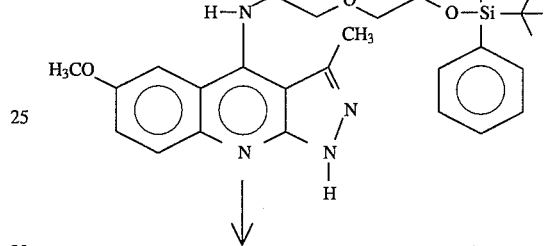

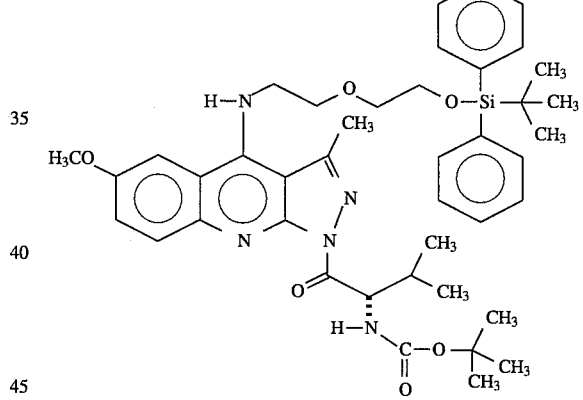

Sodium hydride (60% in oil, 200 mg, 5.0 mmol) was added to a solution of 2-[[2-[(6-methoxy-3-methyl-1H-pyrazolo-[3,4-b]quinolin-4-yl)amino]ethyl]oxy]ethyl]oxy]-[1,1-dimethylethyl-diphenylsilane] (1.0 g, 1.80 mmol) in tetrahydrofuran (20 ml, anhydrous) at 20° C. The resulting reaction mixture was stirred for 20 minutes. t-butoxy carbonyl-L-valine hydroxysuccinimide ester (1.2 g, 3.82 mmol) was then added. The reaction was stirred for 4 hours at ambient temperature, and the Solvent was evaporated.

The residue was extracted with methylene chloride (200 ml), washed with water (100 ml), dried (magnesium sulfate), filtered and the solvent was evaporated to yield an oil which was chromatographed on silica gel with 1/1 (v/v) ethyl acetate/hexanes as the eluant to yield the product as a white foam. MS (FAB m/e M⁺1 (754)

Example 5

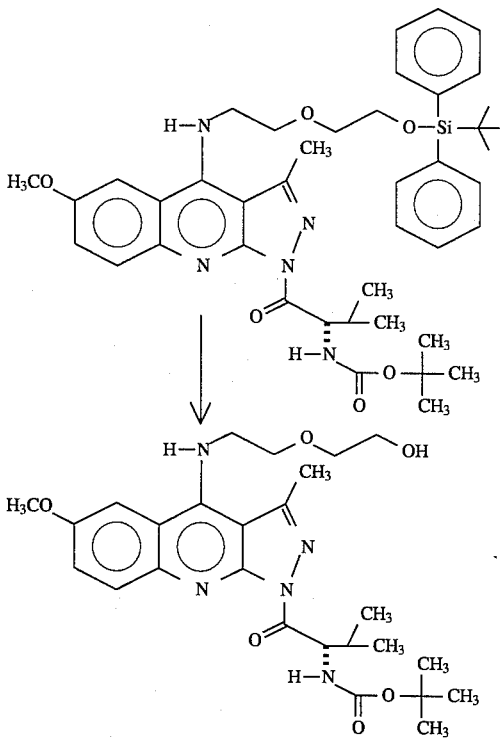

1 normal solution of tetrabutyl ammonium fluoride in tetrahydrofuran (4.0 ml, 4.0 mmol) was added to a solution of the silyl ether (500 mg, 0.663 mmol) in tetrahydrofuran (anhydrous, 10 ml). The resulting reaction mixture was stirred for 2 hours at 20° C. The solvent was evaporated, water (30 ml) was added, and the aqueous layer was extracted with methylene chloride (100 ml). The organic layer, was separated, dried over magnesium sulfate, filtered, and the solvent was evaporated, yielding an oil, which chromatographed on silica gel, eluting with 5% (v/v) methanol:methylene chloride, to yield a pale yellow solid. (300 mg, 88.2% yield) MS(FAB) m/e M⁺1 (516)

Example 6

Step 4

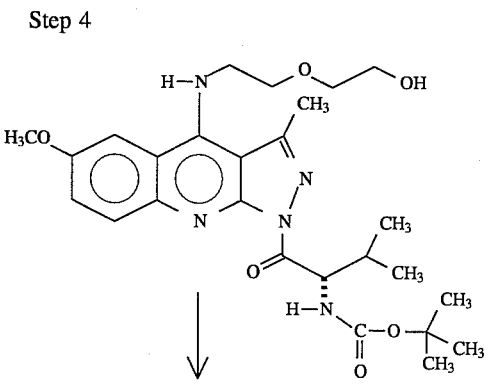

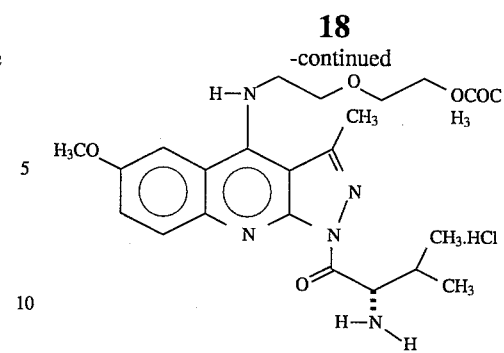

1 Normal hydrogen chloride in acetic acid (10.0 ml) was added to the alcohol (250 mg, 0.485 mmol). The resulting solution was stirred for 30 minutes at 20° C. The solvent was evaporated under reduced pressure. The residue was triturated with ether (3×10 ml). The resultant solid was filtered and washed with ether (10 ml) and dried at 20° C./0.2 mm, yielding the title compound as a yellow powder (204 mg, 93% yield) MS(FAB) m/e M⁺1 (458).

Example 7

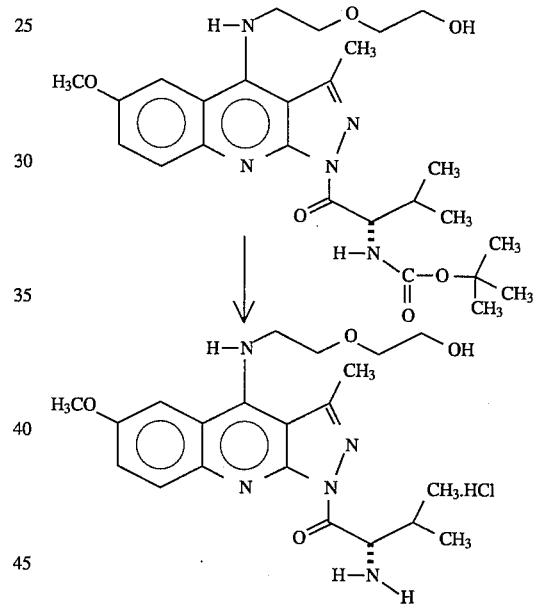

4-[[2-(2-Hydroxyethoxy) ethyl]amino]-6-methoxy-3-methyl- 1-L-valinyl-N-t-butoxy carbonyl-pyrazolo-[3,4-b] quinoline, (300 mg, 0.582 mmol) was stirred in 2 normal hydrogen chloride in dioxane (10.0 ml) for 30 minutes. Ether (25 ml) was added and the resultant precipitate was filtered, washed with ether (10 ml), and dried at 20° C./0.1 mm. to yield the title product as yellow powder, (200 mg, 82.9% yield). MS; CI m/e M⁺1 (416)

Example 8

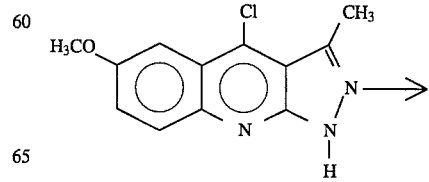

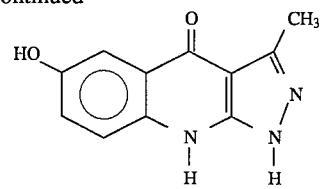

The title compound was prepared as decribed in Example 8 of the copending application Ser. No. U.S. application Ser. No. 08/164,238, filed Dec. 9, 1993 now U.S. Pat. No. 5,459,146 which is hereby incorporated by reference.

Example 9

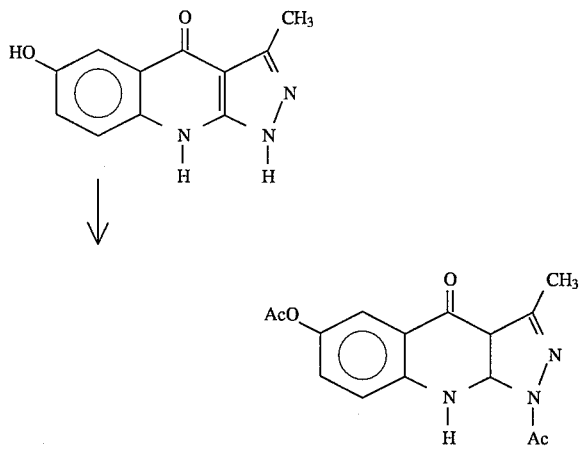

p-Toluene sulfonic acid monohydrate (10 mg, 0.052 mmol) was added to a suspension of 6-hydroxy-4-oxo-3-methyl-1H-pyrazolo-9-H-[3,4-b]quinoline (300 mg, 1.38 mmol) in acetic anhydride (10.0 ml) at 20° C. The reaction mixture was gradually warmed to reflux temperature (125° C.) thereby effecting a solution which was stirred at 125° C. for 1 hour, and then allowed to cool to 20° C. Crystallization occured at 80° C. The resulting white powder, was filtered, washed with acetic anhydride (2×5 ml), water (10 ml) and dried at 60° C./0.2 mm to yield the title compound white powder (350 mg, 84.7% yield). MS (EI (m/e) 299.

Example 10

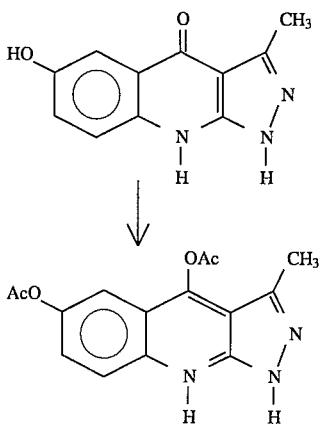

The title compound was prepared as decribed in Example 9 of the copending apllication Ser. No. U.S. application Ser. No. 08/164,238, filed Dec. 9, 1993 now U.S. Pat. No. 5,459,146 which is hereby incorporated by reference.

The title product was obtained as a yellow powder (380 mg, 55.23% yield).

Example 11

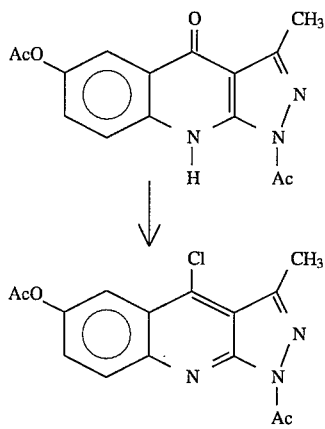

Oxalyl chloride (1.0 ml, 11.46 mmol) was added to a suspension of the acetate (230 mg, 0.77 mmol) in methylene chloride (15 ml) at 20° C. The resulting solution was stirred at 20° C. for 1 hour. A red precipitate was filtered and discarded. The solvent, was evaporated yielding a solid, which on trituration with ether (2×10 ml) and filtration, yielded product as pale yellow powder (230 mg; 94.6% yield). MS EI (m/e M$^+$ 317)

Example 12

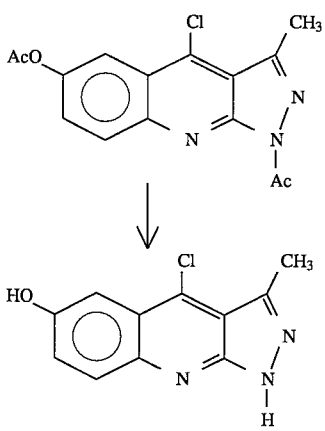

A 10% solution of sodium carbonate in water (30 ml) was added to suspension of the acetate (1.0 g, 3.34 mmol) in methanol (20 ml) at 50° C. The resulting reaction mixture was stirred at 50° C. for 4 hours, then concentrated to about 30 ml volume, diluted to (100 ml) with water, and adjusted to pH 5 with 1 normal hydrochloric acid. The precipitated solid was filtered, washed with water (20 ml), and dried at 50° C./1 mm overnight to yield a yellow powder, (700 mg, 96.5% yield). MS (EI m/e M$^+$233).

Example 13

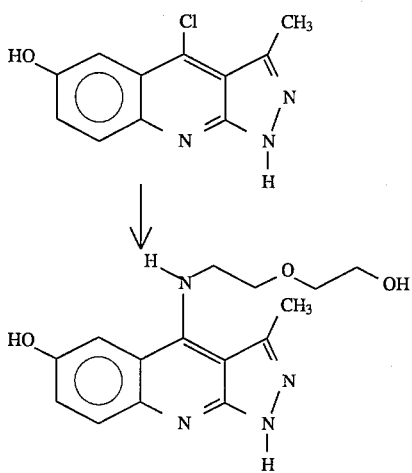

The phenol (150 mg, 0.643 mmol) was added to stirred mixture of 2-(2-aminoethoxy) ethanol (4.0 ml, 39.8 mmol) and sodium hydride (60% in oil, 30 mg. 0.75 mmol). The resulting mixture was then stirred at 110° C. overnight, cooled to 20° C. Water (10 ml) was added and the pH of solution was adjusted to about 7 by addition of 1 normal hydrochloric acid. The solvent was evaporated under high vacuum (40° C./o.5 mm). The residue was dissolved in methanol (30 ml) silica was added (5 g) and the solvent was evaporated. Chromatography on silica gel (Dry Load) with 15% (v/v) methanol: methylene chloride as eluant yielded a product which on recrystallization from methanol: ethyl acetate yielded yellow crystals (120 mg, 62% yield). MS EI m/e M+ 302)

Example 14

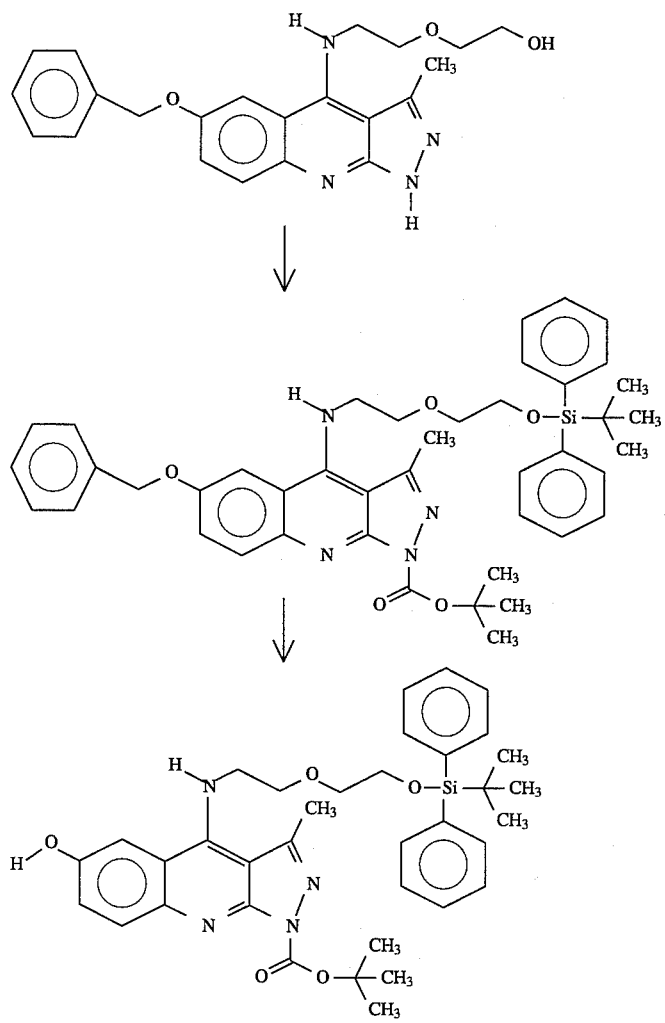

The starting material was prepared by analogy to the procedure of Example 1 as described herein. The title product was obtained as a yellow powder (380 mg, 55.23% yield).

Example 15

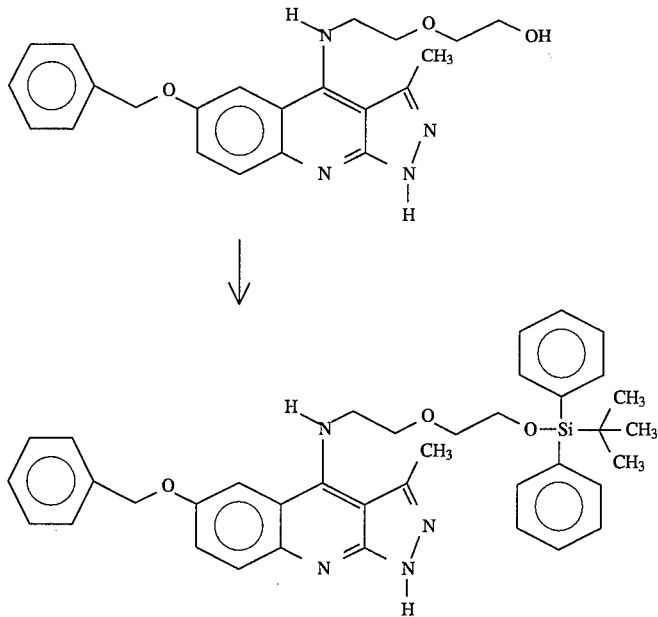

t-Butyl diphenyl silyl chloride (1.0 ml, 3.84 mmol) was added to a solution of the alcohol (500 mg. 1.25 mmol) in dimethylformamide (anhydrous, 10.0 ml) at 20° C. Then imidazole (90 mg, 1.32 mmol) was added. The resulting solution was stirred at 20° C. overnight. The solvent was evaporated under reduced pressure. Water (20 ml), methylene chloride (50 ml) were added. The organic layer was separated, dried over magnesium sulfate (anhydrous), filtered, and the solvent evaporated. The residue was chromatographed on silica gel eluting with 2% (v/v) methanol: methylene chloride. The isolated product was triturated with ether (20 ml) yielding the product as yellow solid. (0.73 g, 90% yield) MS (FAB) m/e M$^+$1 (631)

Example 16

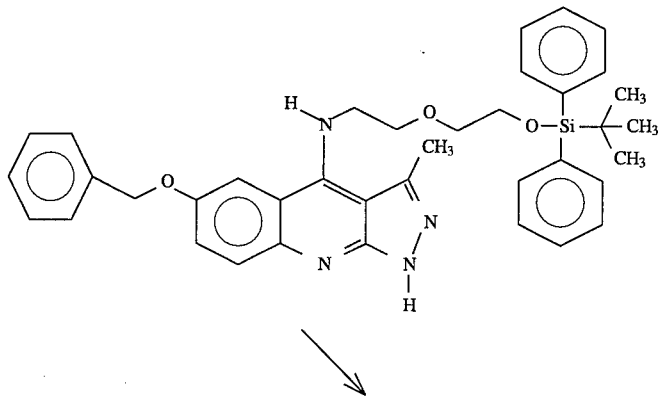

-continued

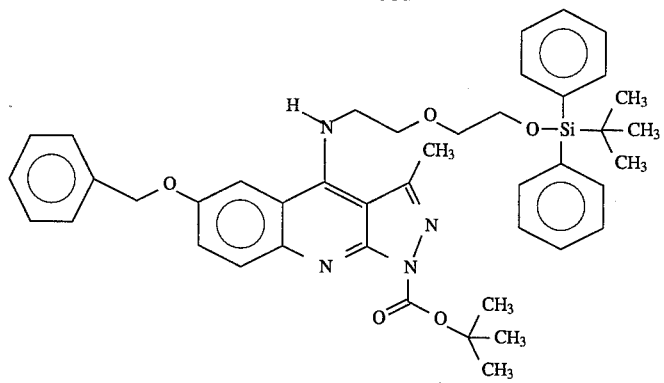

Triethylamine (0.2 ml, 2.72 mmol) was added to a solution of 4-[[2-[((1,1-dimethylethyl) diphenylsilyl) oxy] ethoxy]ethyl]amino]-6-(phenylmethoxy)-3-methyl-1H-pyrazolo-[3,4-b] quinoline - (370 mg, 0.586 mmol) in pyridine (anhydrous, 20 ml) at 20° C. The resulting solution was stirred 15 minutes, then di-tert-butyl dicarbonate (220 mg, 1.009 mmol) was added. The resulting solution was stirred for 30 minutes. The solvent was evaporated, extracted with methylene chloride (100 ml) washed with water (50 ml), dried over magnesium sulfate, filtered, and the solvent was evaporated. Chromatography of the residue on silica gel, eluting with 40:60 (v/v) ethyl acetate: hexanes, yielded the title product as pale yellow powder (350 mg, 81.7% yield) MS FAB (m/e) (M$^+$1, 731).

Example 17

1,4,Cyclohexadiene (1.0 ml, 10.540 mmol) was added to a suspension of Palladium Black (5 mg,) and silyl ether (150 mg, 0.205 mmol) in dimethylformamide (anhydrous, 10 ml). The resulting mixture was stirred at 60° C. for 2 hours, then cooled to 20° C., and the palladium was filtered through a celite pad. The solvent was evaporated. The residue was extracted with methylene chloride (50 ml) washed with water (20 ml) dried over magnesium sulfate, filtered, and the solvent was evaporated to yield an oil which chromatographed on silica gel, eluting with 5% (v/v) methanol: methylene chloride to yield the title product.

The product was further purified by recrystallizing from methylene chloride: acetone: hexanes to yield a white solid (120 mg, 93.3% yield). MS FAB (m/e) (M$^+$1, 641)

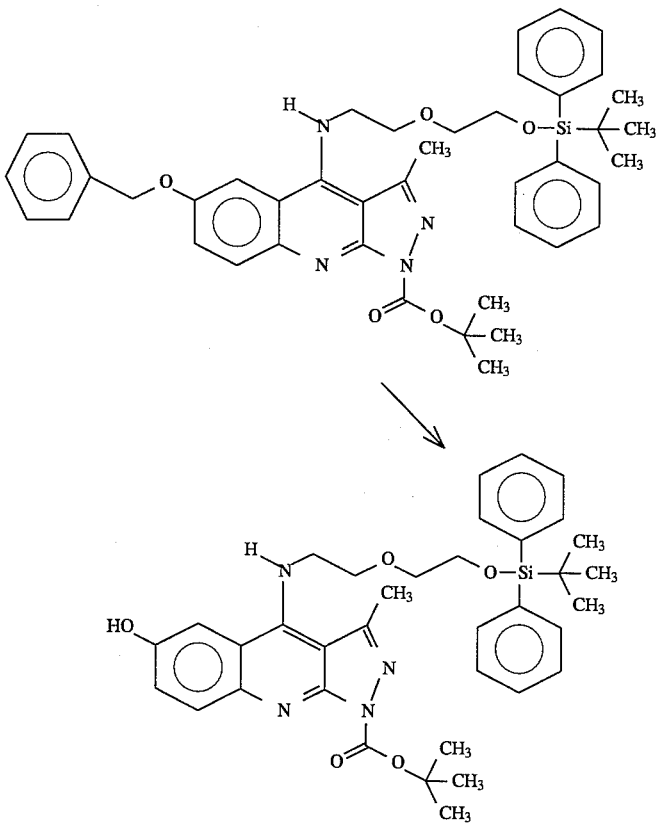

Example 17A

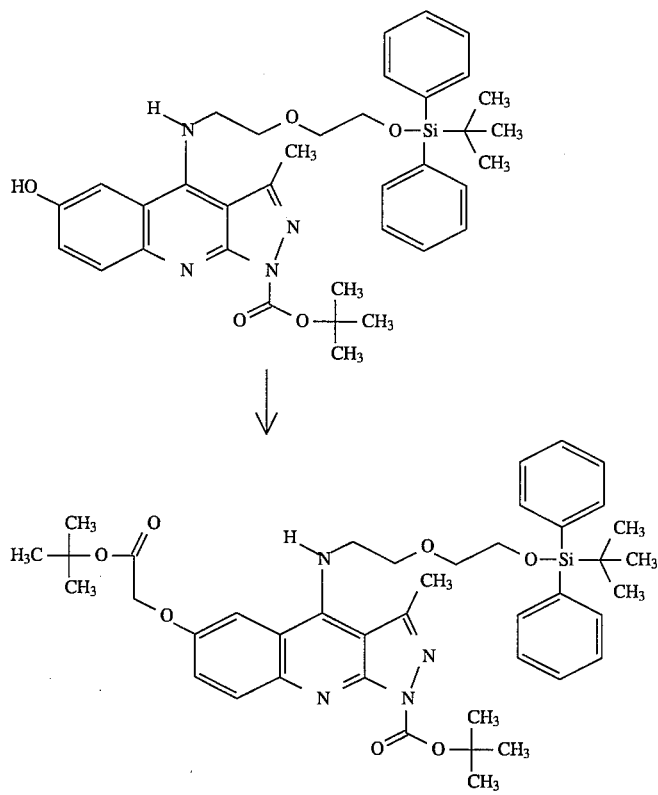

t-Butylbromoacetate (4.2 ml, 26.0 mmol) was added to the phenol (10 g, 15.6 mmol) and potassium carbonate (anhydrous, 4 g, 28.9 mmol) in dimethylformamide (anhydrous, 100 ml) at 20° C. The so-formed mixture was stirred for 4 hours, then the solvent was evaporated and the residue was extracted with ether (300 ml), washed with water, dried over magnesium sulfate, filtered and evaporated, yielding an oil. The oil was dried at 0.2 mm and when the oil solidified it was triturated with hexanes (3×20 ml) and filtered to yield the product as a white powder. mp 108°–109° C., MS; FABS m/e (M$^+$1, 755).

The preparation of the starting phenol is described in example 17 of the present specification.

Example 17B

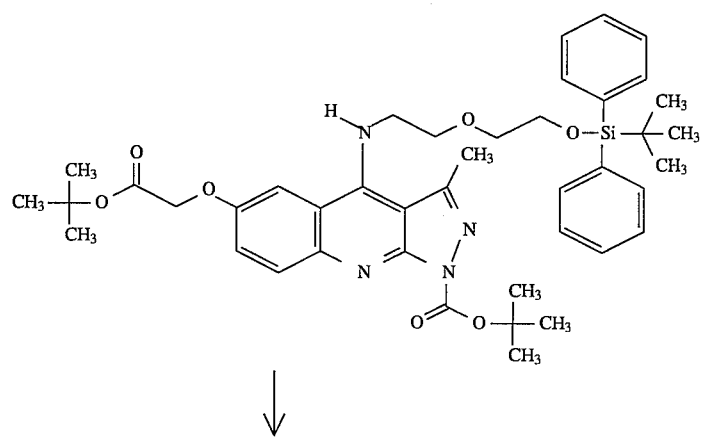

-continued

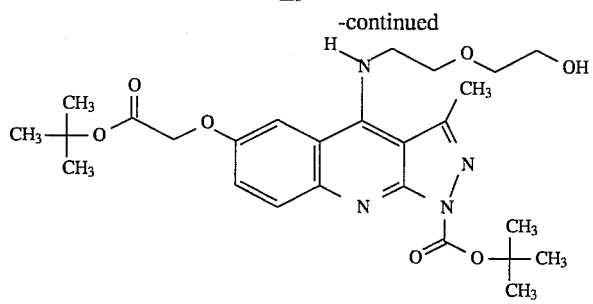

Tetrabutyl ammonium flouride (1.0M in tetrahydrofuran, 20.0 ml, 20 mmol) was added to a solution of the silyl ether (11 g, 14.5 mmol) in tetrahydrofuran (anhydrous, 300 ml). The resulting reaction mixture was stirred for two hours. The solvent was evaporated. The residue was extracted with methylene chloride (300 ml), washed with water (200 ml), dried over magnesium sulfate, and filtered. The solvent was evaporated, and the residue was triturated with acetone:hexanes (1:10, 50 ml) to yield the product as cream colored solid. mp 146° C.–148° C.), MS m/e FABS (517, $M^+1$).

Example 17C

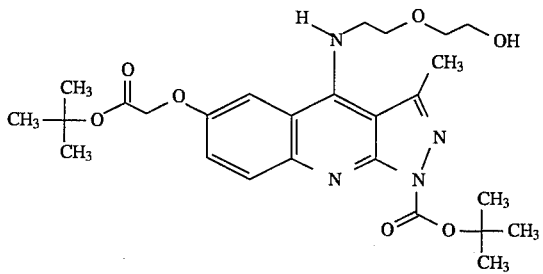

The t-butyl ester (10 g, 19.3 mmol) was stirred in trifluoroacetic acid (100 ml) for two hours. The solvent was evaporated and the residue was extracted with chloroform (200 ml). The solvent was re-evaporated, the residual solid was was dissolved in 10% sodium bicarbonate solution (100 ml), and then the pH was slowly adjusted to 4.5 with 10% citric acid (about 50 ml). The precipitate was filtered, washed with water (200 ml), and dried at 60° C./0.2 mm) to yield the product as a yellow solid, MS FAB m/e ($M^+1$, 361).

Example 17D

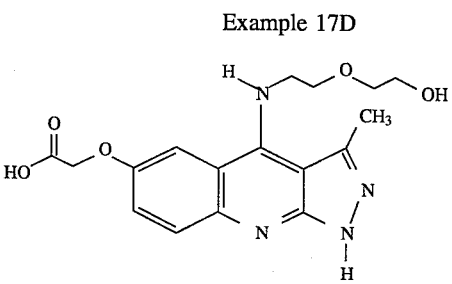

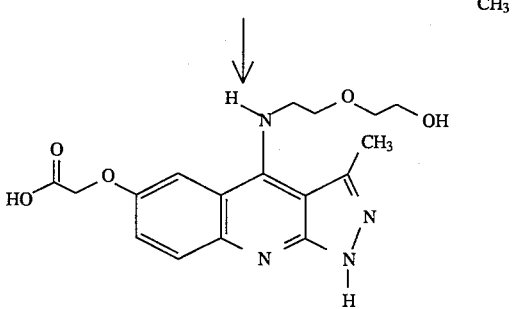

A solution of sodium bicarbonate (1.4 g, 16.6 mmol) in water (20 ml) was added to a solution of the carboxylic acid (6.0 g, 16.6 mmol) in methanol (300 ml) at 20° C. The resulting solution was stirred for 20 minutes and then the solvent was evaporated. The residue was triturated with acetone (100 ml) and filtered. The yellow solid was dried at 60° C./0.05 mm) and recrystallized from acetone-water to yield the title compound as a yellow powder (4.8 g, MS FAB ($M^+1$, 383).

Example 18

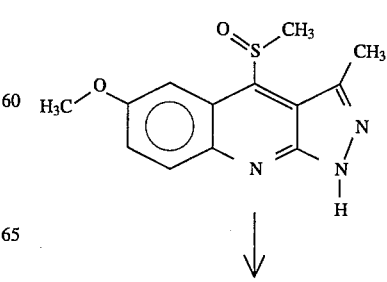

-continued

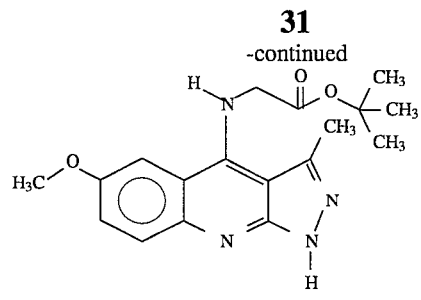

Sodium hydride (60% in oil; 182 mg, 4.55 mmol) was added to a suspension of t-butylglycine hydrochloride (800 mg, 4.55 mmol) in tetrahydrofuran (anhydrous, 80 ml). The resulting mixture was stirred for 30 minutes, then the sulfoxide (500 mg, 1.818 mmol), was added, the reaction mixture was refluxed overnight, and cooled to 20° C. Water (10 ml), was added, the precipitated solid was filtered and washed with tetrahydrofuran (10 ml). The filtrate was evaporated, and water (50 ml) was added to the residue. The insoluble powder, was filtered, washed with water (10 ml) dried at 60° C./0.2 mm, then chromatographed on silica gel using 4% (v/v) methanol: methylene chloride as eluant to yield a product which on trituration with ether (2×5 ml) gave the title compound (510 mg, 82.1% yield) as a yellow powder.

MS EI (m/e) M$^+$, 342

The starting sulfoxide was prepared as described in the copending application Ser. No. 08/164,178, now abandoned (Attorney's Docket No. IN0011-1) which is hereby incorporated by reference.

Example 19

Step 2

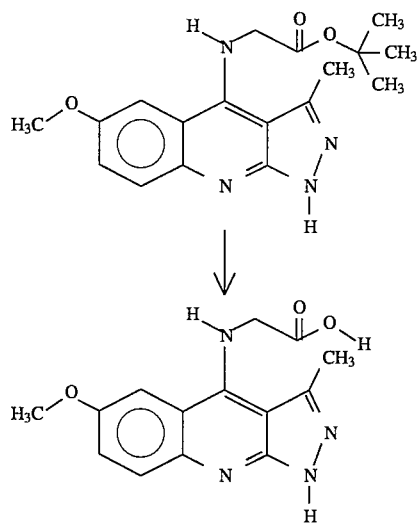

A solution of the ester (450 mg. 1.315 mmol) was stirred in trifluoroacetic acid (5.0 ml) for 1 hour. The solvent was evaporated, chloroform (15 ml) was added and the solvent was re-evaporated. The residue was extracted with 10% sodium bicarbonate solution (40 ml) washed with ether (15 ml) and then acidified with 2N HCl (to pH 3). The pH was raised to 5 by slow addition of 10% sodium bicarbonate solution and allowed to stand overnight at room temperature. Yellow solid precipitate was filtered, washed with water (10 ml), and dried at 60° C./0.2 mm.

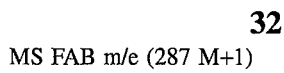
MS FAB m/e (287 M+1)

Example 20

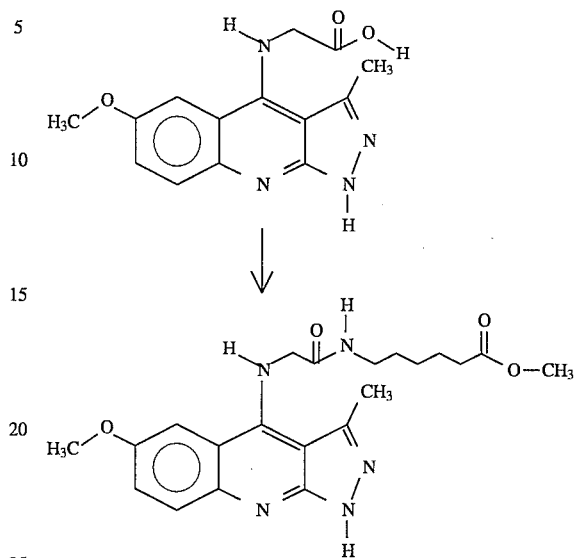

1-(3-dimethyl aminopropyl)-3-ethyl carbodiimide hydrochloride (EDCI: 60 mg, 3.14×10$^{-4}$M) and 1-hydroxybenzotriazole (HOBT) monohydrate (60 mg, 4.44×10$^{-4}$M) were added to a suspension of the acid 60 mg, 2.097×10$^{-4}$M) in dimethylformamide (anhydrous, 10 ml) at 0° C. e-amino caproic acid methyl ester hydrochloride (50 mg, 3.44×10$^{-4}$M) and triethylamine (0.3 ml, 4.09×10$^{-4}$M) were then added. The resulting mixture was stirred overnight at 20° C. The solvent was evaporated, the residue was extracted with methylene chloride (60 ml), washed with water (10 ml), dried over magnesium sulfate, filtered, and the solvent was evaporated yielding an oil. The oil chromatographed on silica gel, eluting with 3%–7% v/v methanol: methylene chloride to yield the title product.

MS EI m/e (M$^+$ 413)

Example 21

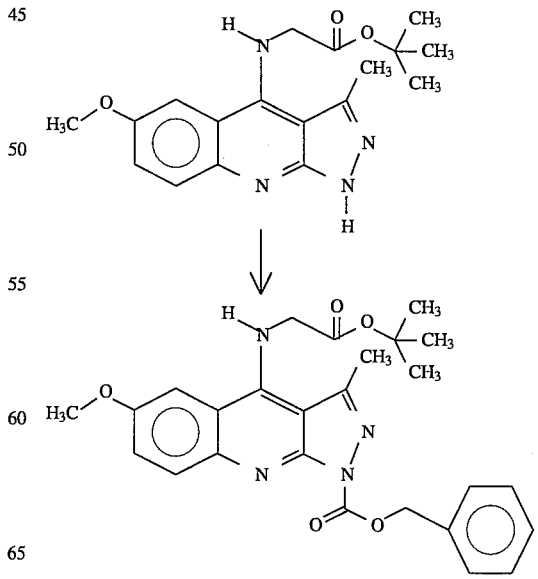

Pyridine (anhydrous, 3.0 ml, 38.77 mmol) was added to suspension of the t-butyl ester (1.0 g, 2.92 mmol) in tetrahydrofuran (anhydrous, 50 ml) at 0° C. Then benzyl chloroformate (1.0 ml, 7.0 mmol) and triethylamine (1.0 ml, 7.18 mmol) were added. The reaction mixture was stirred for 1 hour at 0° C., then overnight at room temperature. The solvent, was evaporated, the residue was extracted with methylene chloride (100 ml), washed with water (100 ml) dried over magnesium sulfate, filtered and evaporated to yield an oil. The oil was dried at 0.1 mm and solidified and trituration of the solid with hexanes yielded the product as white solid. (0.96 g, 69.06% yield).

MS; EI (m/e) M$^+$ 476)

Example 22

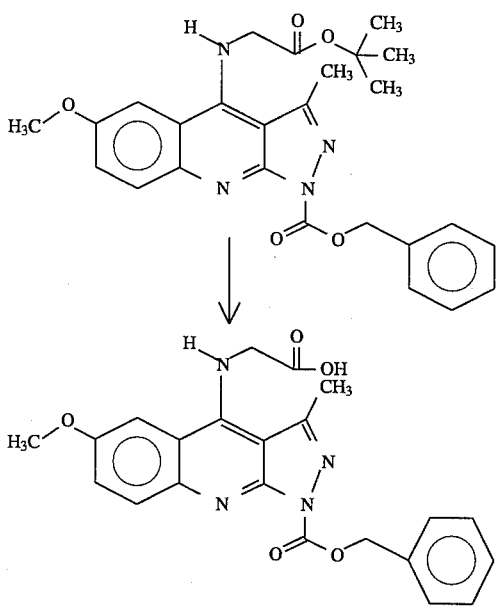

A solution of the t-butyl ester (600 mg, 1.26 mmol) was stirred in trifluoroacetic acid (10 ml) at 0° C., for 10 minutes, then at room temperature for 1 hour. The solvent was evaporated and water was added. (20 ml). The precipitate was filtered, washed with water (20 ml), dried at 60° C./0.5 mm. (525 mg, 99.05% yield). MS EI (m/e) M$^+$1 (421.2)

Example 23

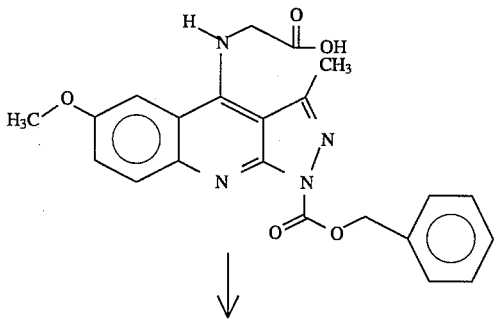

A solution of sodium bicarbonate (20 mg. 0.238 mmol) in water (1.0 ml) was added to a solution of the acid (100 mg, 0.238 mmol) in methanol (25 ml) at 20° C. The resulting mixture was stirred for 10 minutes. Insoluble solids, were filtered, the filtrate was concentrated and the residue was triturated with acetone (5 ml); The precipitated solid was filtered, washed with ether (10 ml) dried at 60° C./0.5 mm.) to yield the title product (20 mg, 94.8% yield). MS FAB m/e M$^+$23 (465) M$^+$1 (443)

Example 24

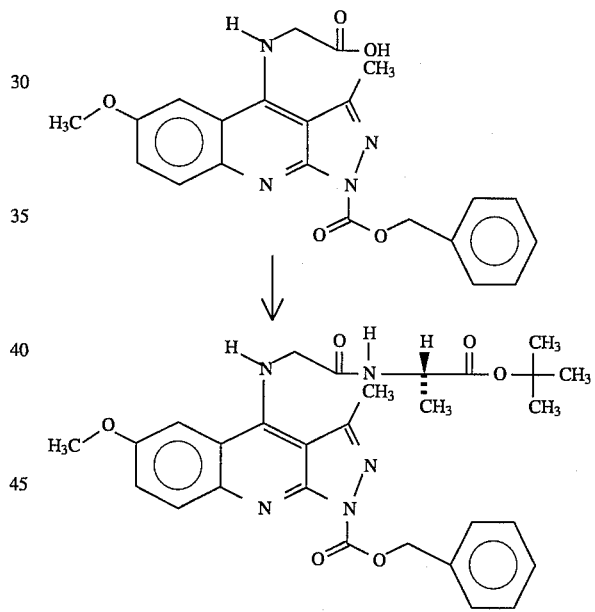

1-(3-dimethyl aminopropyl)-3-ethyl carbodiimide hydrochloride (EDCI) (700 mg, 3.66 mmol) and 1-hydroxybenzotriazole (HOBT) monohydrate (60 mg, 4.44 mmol) were added to a solution of the acid (700 mg, 1.58 mmol) in dimethylformamide (anhydrous, 15 ml) at 0° C. L-Alanine t-butylester, hydrochloride (700 mg 3.85 mmol) and triethylamine (0.5 ml, 6.818 mmol) were added. The resulting mixture was stirred for 1 hour at 0° C., then overnight at room temperature. The dimethylformamide was evaporated, the residue was extracted with methylene chloride (60 ml), washed with water (20 ml) dried over magnesium sulfate, filtered and the solvent was evaporated. The residue was chromatographed on silica gel, eluting with 4% (v/v) methanol: methylene choride to give a solid, which recrystallized from acetone: hexanes yielding a white solid (350 mg, 40.4% yield). MS FAB m/e (M$^+$1, 548.7).

Example 25

The following compound was prepared:

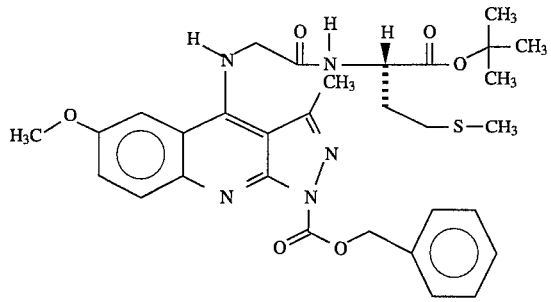

using a similar method as in the example just above except that an equivalent quantity of L-methionine t-butyl ester hydrochloride was substituted for the L-alanine. The title compound was a pale yellow powder.: % yield is 57.39. MS FAB m/e (M+1, 608.6)

Example 26

The following compound was prepared:

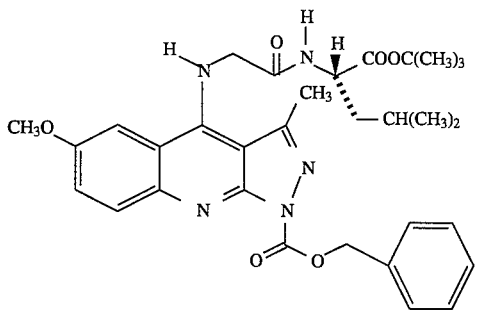

using a similar method as in the example just above except that an equivalent quantity of L-leucine t-butyl ester was substituted for the L-methionine. MS FAB m/e M⁺1, 590.7) yield is 54.26%.

Example 27

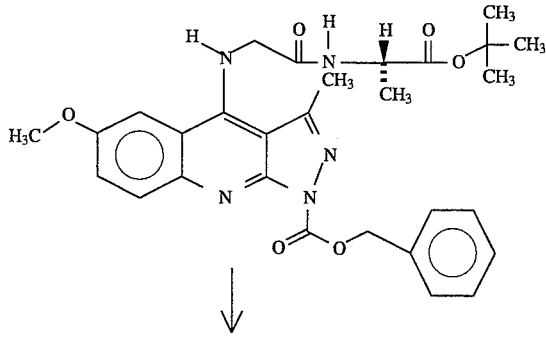

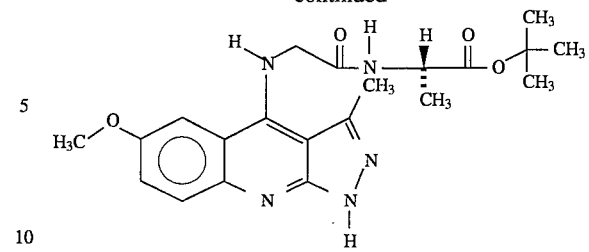

Palladium (black) 10 mg, and 1,4 cyclohexadiene (0.2 ml, 2.94 mmol) were added to a solution of t-butyl ester (250 mg, 0.455 mmol) in dimethylformamide (3 ml, anhydrous) at room temperature, then stirred at 60° C. for twenty minutes. The mixture was cooled to room temperature, filtered through a celite pad washed with dimethyl formamide (3 ml), and the solvent was evaporated. The residue chromatographed on silica gel, eluting with 5–8% (v/v) methanol: methylene chloride—(column was pretreated with 1% triethylamine in 5% (v/v) methanol: methylene chloride) yielding the title compound as yellow solid (165 mg, 87% yield). MS FAB m/e (M⁺1, 414.3)

Example 28

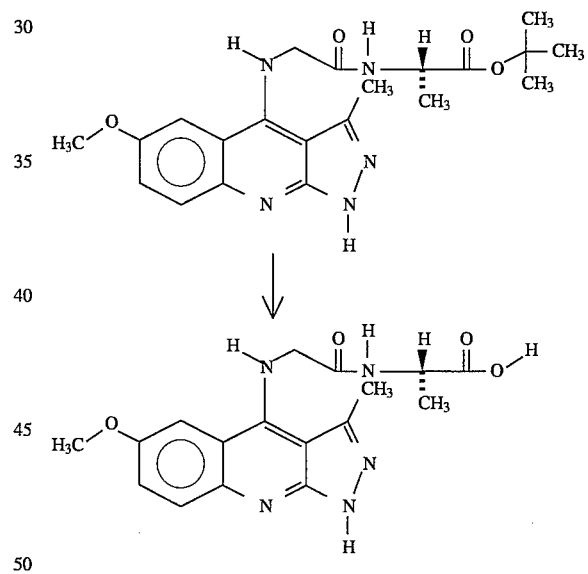

A solution of the t-butyl ester ((120 mg, $0.290 \times 10^{-4}$ M) was stirred in trifluoracetic acid (5.0 ml) at 20° C. for 1 hour. The solvent, was evaporated, chloroform was added (10 ml) and the solvent re-evaporated. The residue was triturated with acetone:hexanes (1:5), the precipitated solid washed with ether (2×10 ml), dried at 20° C./0.2 mm. (81.7% yield) MS FAB (m/e) (358, M⁺1)

Example 29

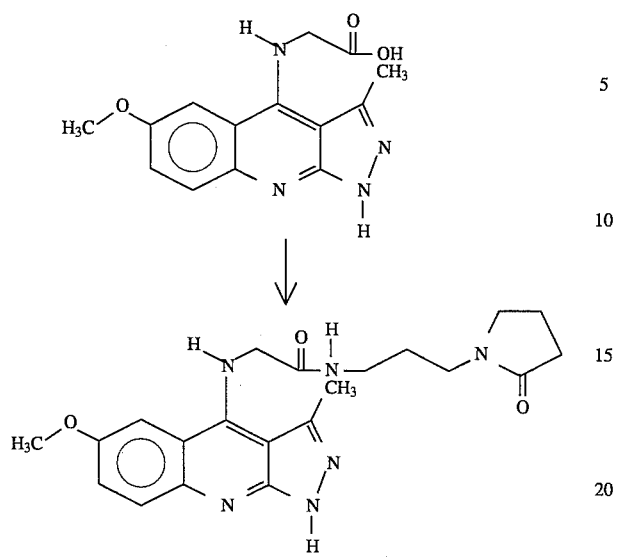

1-(3-dimethylamino propyl)-3-ethyl carbodiimide hydrochloride (EDCI) (120 mg, 0.628 mmol) and 1-hydroxy benzotriazole (HOBT) monohydrate (100 mg, 0.740 mmol) were added to a solution of the acid shown just above (130 mg, 0.454 mmol) in dimethyl formamide (anhydrous, 5 ml) at 5° C. The resulting mixture was stirred 30 minutes at 5° C., 1-(3-aminopropyl-2-pyrollidinone (0.5 ml, 3.56 mmol:) was added and the resulting mixture was stirred overnight at 20° C. The dimethyl formamide was evaporated, water (20 ml) and methylene chloride (70 ml) were added. The organic layer was separated and the aqueous layer was extracted with methylene chloride (2×100 ml). The organics were combined, dried over magnesium sulfate, filtered and the solvent was evaporated, yielding an oil, which crystallized from—acetone; hexanes (v/v) 5 ml: 10 ml on standing at 0° C. overnight. Yellow crystals were filtered, washed with hexanes (10 ml) and dried at 60° C./0.1 mm. (98 mg, 52.68% yield).

Example 30

Using a similar procedure the following compound was prepared:

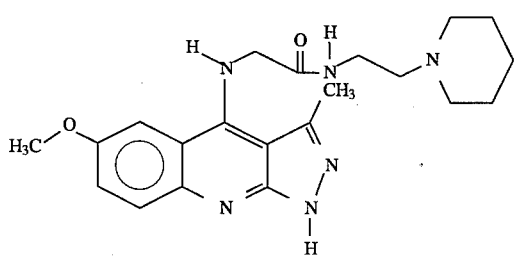

An equivalent quantity of 1-(2-aminoethyl)piperidine (98%) was used inplace of the pyrollidinone to prepare the title compound. M.p. 186°–187° C. MS FAB m/e ($M^+1$ 397)

Example 31

Using a similar procedure the following compound was prepared:

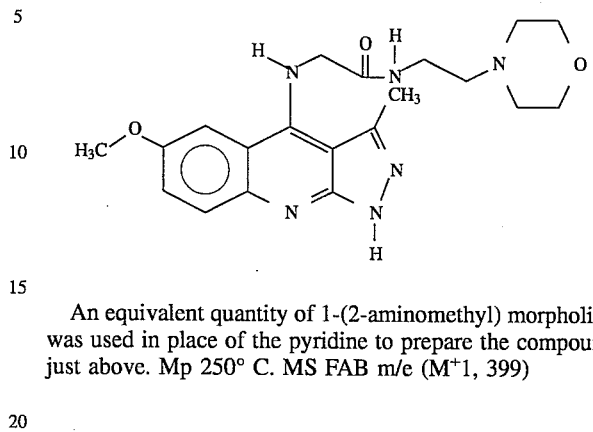

An equivalent quantity of 1-(2-aminomethyl) morpholine was used in place of the pyridine to prepare the compound just above. Mp 250° C. MS FAB m/e ($M^+1$, 399)

Example 32

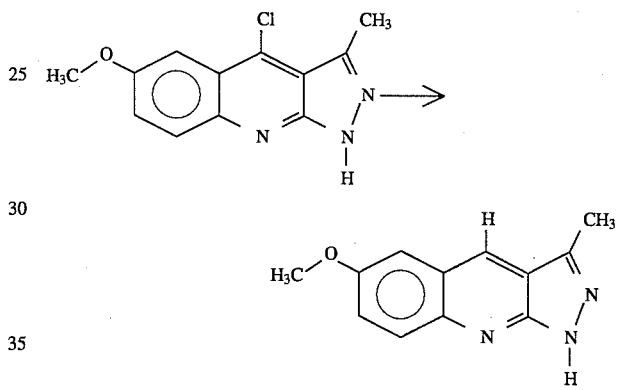

Palladium black (10 mg) and 1,4 cyclohexadiene (0.2 ml, 2.94 mmol) were added to a solution of the chloride containing compound shown just above (250 mg, 1.01 mmol) in dimethylformamide (anhydrous, 5 ml) at 20° C. then stirred at 70° C. for 5 hours. The reaction mixture was cooled to room temperature, filtered through a celite pad, and the solvent was evaporated. The residual solid was stirred in water (5 ml), and the insoluble solids were filtered. The solids were suspended in water (10 ml), basified with 10% sodium bicarbonate (to pH 8). The precipitate was filtered, washed with water (5 ml) and dried at 60° C./0.1 mm. A solid was obtained, which chromatographed on silica gel eluting with 3% (v/v) methanol:methylene chloride yielding the title product as pale yellow powder. MS CI (214. $M^+1$) (171 mg, 80% yield.

Example 33

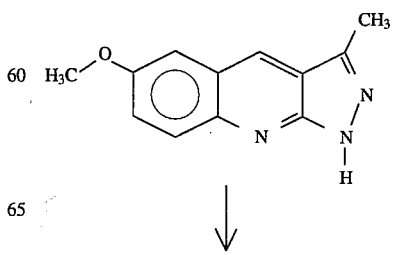

-continued

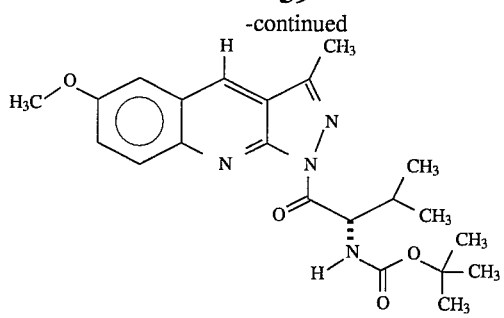

Sodium hydride was added (60% in oil, 110 mg, 2.75 mmol) to suspension of the staring pyrazoloquinoline compound. (500 mg, 2.34 mmol) in tetrahydrofuran (anhydrous, 50 ml) at 20°. The resulting mixture was stirred for 30 minutes then N-a-t-BOC-L-valine-N-hydroxysuccinimide ester (710 mg, 2.38 mmol) was added. The resulting mixture was stirred for 4 hours at 20° C. then the solvent was evaporated. Water (20 ml) and methylene chloride (50 ml) were added. The organic layer, was separated dried over magnesium sulfate, filtered, and the solvent evaporated. The residue was chromatographed on silica gel eluting with 1:1 (v/v) ethyl acetate: hexanes yielding the title product as a white powder (505 mg, 68.80% yield).

MS FAB m/e (397, M$^+$1) for $C_{22}H_{28}N_4O_3$.

Example 34

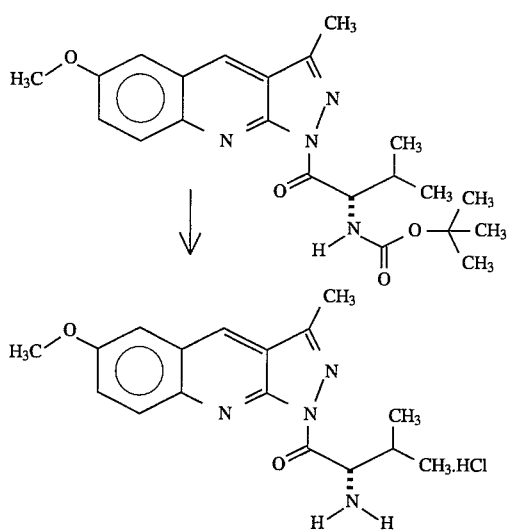

1 Normal hydrogen chloride in acetic acid (40 ml) was added to the pyrazoloquinoline (9.0 g, 22.7 mmol) and the resulting solution was stirred for 10 minutes.

The solvent was evaporated under reduced pressure. Ether (100 ml), was added, the precipitate was filtered, washed with ether, dried at 20° C./0.1 mm/Hg to yield (6.5 g, 91.67%) product as yellow powder. MS FAB m/e (313, M$^+$1).

Using similar procedures as in the preparation just above, the following analog was synthesized:

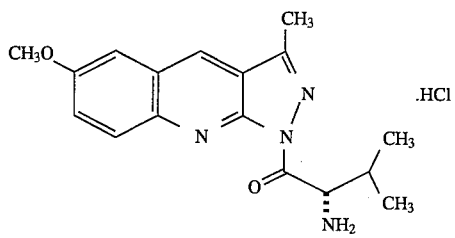

Example 35

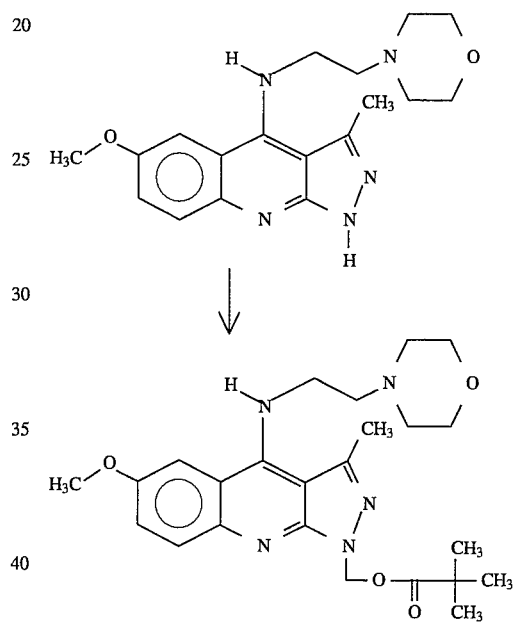

Sodium hydride (60% in oil; 1.12 g, 28.1 mmol) was added to a solution of the morpholino compound (9.0 g, 26.4 mmol) in dimethyl formamide (anhydrous, 130 ml) at 20° C. The resulting solution was stirred for 30 minutes, then chloromethyl pivalate (10.0 ml), was added and the reaction mixture was stirred for 3 hours at 20° C. The reaction mixture was concentrated to about 50 ml, water (100 ml) was added. The precipitated solid was filtered, washed with water (100 ml), triturated with hexanes (3×50 ml) and dried at 20° C./0.5 mm. yielding the title product as a pale yellow solid (9.4 g, 78.3%).

MS m/e (EI 455.2, M$^+$).

Compounds prepared by methods analogous to those set forth in Example 1 are as follows:

| Compound | | Molecular Formula | Mass Spectral Data |
|---|---|---|---|
| (1) | [structure] | $C_{16}H_{20}N_4O_3$ | CI (M$^+$1, 317) |
| (2) | [structure] | $C_{16}H_{16}N_4O_2$ | EI (M$^+$, 272) |
| (3) | [structure] | $C_{18}H_{23}N_5O_2$ | EI (M$^+$, 341) |
| (4) | [structure] | $C_{19}H_{19}N_5O$ | EI (M$^+$, 333) |
| (5) | [structure] | $C_{15}H_{18}N_4O_2$ | CI (M$^+$1, 287) |

-continued

| Compound | Molecular Formula | Mass Spectral Data |
|---|---|---|
| (6) | $C_{19}H_{26}N_4O_4$ | EI (M+, 374) |
| (7) | $C_{16}H_{21}N_5O_2$ | CI (M+1, 316) |
| (8) | $C_{17}H_{22}N_4O_2$ | EI (M+, 314) |
| (9) | $C_{15}H_{18}N_4O_3$ | EI (M+, 302) |
| (10) | $C_{17}H_{22}N_4O_3$ | EI (M+, 330) |
| (11) | $C_{17}H_{22}N_4O_3$ | CI (M+1, 331) |

-continued
| Compound | Molecular Formula | Mass Spectral Data |
|---|---|---|
| (12) 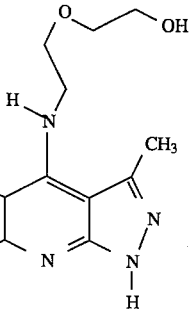 | $C_{22}H_{24}N_4O_3$ | CI (M$^+$1, 393) |
| 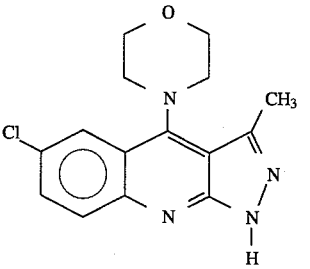 | $C_{15}H_{15}N_4ClO$ | EI (M$^+$, 302) |
Compounds prepared by methods analogous to those set forth in the examples contained herein are as follows:
| Compound | Molecular Formula | Mass Spectral Data |
|---|---|---|
| (13) 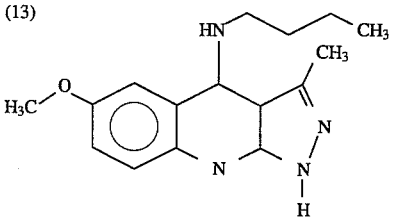 | $C_{16}H_{20}N_4O$ | EI (M$^+$, 284) |
| (14) 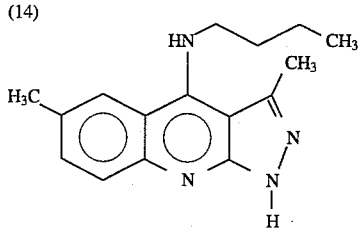 | $C_{16}H_{20}N_4$ | EI (M$^+$, 268) |
| (15) 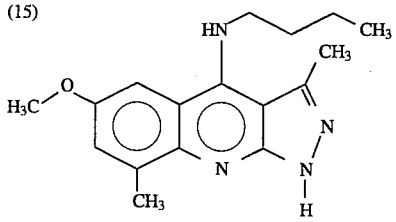 | $C_{17}H_{22}N_4O$ | EI (M$^+$, 298) |

-continued
| Compound | Molecular Formula | Mass Spectral Data |
|---|---|---|
| (16)  | $C_{17}H_{23}N_5O$ | EI (M⁺, 313) |
Compounds prepared by methods analogous to those set forth in Example 2 are as follows (amino acid examples):
| Compound | Molecular Formula | Mass Spectral Data |
|---|---|---|
| (17) | $C_{17}H_{20}N_4O_2 \cdot HCl$ | FAB (313), M⁺1) |
| (18) | $C_{15}H_{16}N_4O_2 \cdot HCl$ | FAB (285, M⁺1) |
| (19) | $C_{23}H_{32}N_6O_3 \cdot 2HCl$ | FAB (441, M⁺1) |
| (20) | $C_{15}H_{16}N_4O_2 \cdot HCl$ | FAB (285, M⁺1) |

-continued

| Compound | Molecular Formula | Mass Spectral Data |
|---|---|---|
| (21) | $C_{16}H_{18}N_4O_2 \cdot HCl$ | Cl (299, M$^+$1) |
| (22) | $C_{18}H_{22}N_4O_2 \cdot HCl$ | Cl (327, M$^+$1) |

What is claimed is:

1. A compound of the formula

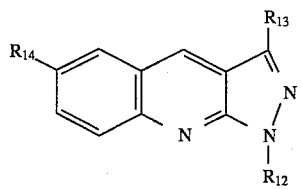

or a pharmaceutically acceptable salt thereof, wherein $R_{12}$ is —CO—$R_{15}$, wherein $R_{15}$ is ($C_1$–$C_8$)alkyl substituted by $NH_2$ or —$CH_2$—$NHR_{16}$ wherein $R_{16}$ is ($C_1$–$C_4$) alkyl;

$R_{13}$ is ($C_1$–$C_8$)alkyl; and $R_{14}$ is ($C_1$–$C_8$)alkoxy.

2. A compound of the formula

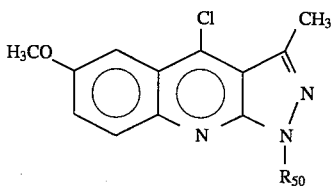

wherein $R_{50}$ is a residue of an α-amino acid; or a pharmaceutically acceptable salt thereof.

3. A compound according to claim 2 selected from the group consisting of

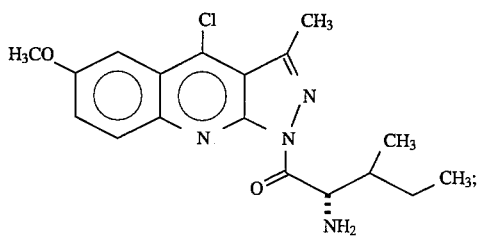

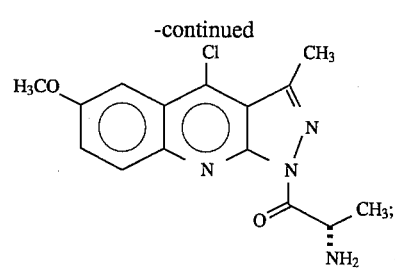

and

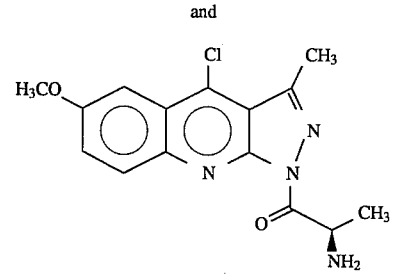

or a pharmaceutically acceptable salt thereof.

4. A compound of the formula:

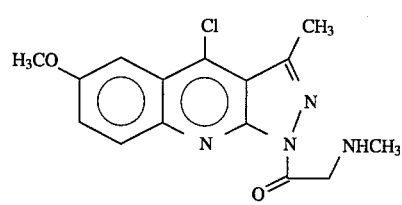

or a pharmaceutically acceptable salt thereof.

* * * * *